(12) United States Patent
Zhou et al.

(10) Patent No.: US 12,595,460 B2
(45) Date of Patent: Apr. 7, 2026

(54) METHOD AND APPARATUS FOR PRODUCING CAR T CELLS

(71) Applicant: Applied Cells Inc., Santa Clara, CA (US)

(72) Inventors: Yuchen Zhou, San Jose, CA (US); Silin Sa, San Jose, CA (US); Liping Yu, San Jose, CA (US); Fengxiang Pang, Qinhuangdao (CN); Jinlong Fan, Qinhuangdao (CN); Jimeng Zhu, Qinhuangdao (CN); Huiyu Wang, Shanghai (CN)

(73) Assignee: Applied Cells Inc., Santa Clara, CA (US)

( * ) Notice: Subject to any disclaimer, the term of this patent is extended or adjusted under 35 U.S.C. 154(b) by 0 days.

(21) Appl. No.: 19/070,308

(22) Filed: Mar. 4, 2025

(65) Prior Publication Data

US 2025/0313795 A1 Oct. 9, 2025

Related U.S. Application Data

(60) Provisional application No. 63/575,518, filed on Apr. 5, 2024.

(51) Int. Cl.

| | |
|---|---|
| *C12N 5/0783* | (2010.01) |
| *C12M 1/00* | (2006.01) |
| *C12N 15/86* | (2006.01) |

(52) U.S. Cl.
CPC ............ *C12M 47/02* (2013.01); *C12M 23/38* (2013.01); *C12M 29/00* (2013.01); *C12N 5/0636* (2013.01); *C12N 15/86* (2013.01); *C12N 2510/00* (2013.01); *C12N 2740/10043* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 9,856,563 B2 | 1/2018 | Martinson et al. | |
| 10,144,770 B2 | 12/2018 | Campana | |
| 10,620,212 B2 | 4/2020 | Miltenyi et al. | |
| 10,696,961 B2 | 6/2020 | Zhang et al. | |
| 10,844,353 B2 | 11/2020 | Ward et al. | |
| 11,781,113 B2 | 10/2023 | Shi et al. | |

| | | | |
|---|---|---|---|
| 2013/0330739 A1* | 12/2013 | Yu | B03C 1/0332 |
| | | | 435/7.1 |
| 2017/0037370 A1* | 2/2017 | Kaiser | C12N 5/0636 |
| 2019/0270084 A1 | 9/2019 | Zhou | |
| 2022/0072548 A1 | 3/2022 | Yen et al. | |
| 2022/0340932 A1 | 10/2022 | Waters et al. | |
| 2022/0364055 A1 | 11/2022 | Treanor et al. | |
| 2023/0027004 A1 | 1/2023 | Freund et al. | |
| 2023/0338968 A1 | 10/2023 | Zhou | |
| 2024/0024360 A1 | 1/2024 | Fachin et al. | |

FOREIGN PATENT DOCUMENTS

| | | |
|---|---|---|
| WO | 2015162211 | 10/2015 |
| WO | 2018106732 | 6/2018 |
| WO | 2020047452 | 3/2020 |

OTHER PUBLICATIONS

Warda, W. et al., Cancer Res., 2019, vol. 79: pp. 663-675.*
Warda, W. et al., Cancer Res., 2019, Supplementary data, 9 pages.*
Warda, W. et al., Cancer Res., 2019, Supplementary Fig. 2, 1 page.*
Abou-El-Enein et al., Scalable manufacturing of CART T cells for cancer immunotherapy, Blood Cancer Discovery, Sep. 2021, pp. 408-422.
Ghassemi et al., Rapid manufacturing of non-activated potent CAR T cells, Nature Biomedical Engineering, Feb. 2022, pp. 118-128, vol. 6.
Nicod et al., CAR-T cells targeting IL-1RAP produced in a closed semiautomatic system are ready for the first phase I clinical investigation in humans, Current Research in Translational Medicine, Feb. 2023, 103385, vol. 71.
Lonez et al., Allogeneic CAR-T therapy technologies: has the promise been met?, Cells, Jan. 2024, 146, vol. 13.
Harrer et al., Magnetic CAR T cell purification using an anti-G4S linker antibody, Journal of Immunological Methods, Apr. 2024, 113667, vol. 528.

(Continued)

*Primary Examiner* — Michael D Burkhart
(74) *Attorney, Agent, or Firm* — Bing K. Yen

(57) ABSTRACT

A method for producing a population of T cells that express a chimeric antigen receptor (CAR) comprising the steps of providing a fluid sample including a population of T cells; labeling the population of T cells with magnetic beads; extracting the population of T cells from the fluid sample by flowing the fluid sample through a first conduit that passes through a first magnetic separator device; transducing the population of T cells to express a chimeric antigen receptor (CAR) by contacting the population of T cells with a population of lentivirus in a solution contained in an incubation container; and harvesting the population of T cells by flowing the solution through a second conduit that passes through a second magnetic separator device, wherein the first conduit, the incubation container, and the second conduit are fluidically connected by a network of fluidic lines.

2 Claims, 20 Drawing Sheets

(56)          References Cited

OTHER PUBLICATIONS

Jackson et al., Automated manufacture of autologous CD19 CAR-T cells for treatment ofFrontiers in Immunology, Aug. 2020, 1941, vol. 11.

Mock et al., Automated manufacturing of chimeric antigen receptor T cells for adoptive immunotherapy using CliniMACS Prodigy, Cytotherapy, 2016, pp. 1002-1011, vol. 18.

Ahmadi et al., Accelerating CAR T cell manufacturing with an automated next-day process, Current Research in Translational Medicine, 2025, 103489, vol. 73.

Extended European Search Report for Application No. 25168658.0, Aug. 25, 2025.

* cited by examiner

METHOD AND APPARATUS FOR PRODUCING CAR T CELLS

CROSS-REFERENCE TO RELATED APPLICATIONS

The present application claims priority to provisional application No. 63/575,518, filed on Apr. 5, 2024, the content of which is incorporated herein by reference in its entirety.

BACKGROUND OF THE INVENTION

The present invention relates to production of CAR T cells, and more particularly, to a method and apparatus for producing the same cells.

Immunotherapy involving T cells that are engineered to express chimeric antigen receptors (CAR) has become an important treatment option for patients with B-cell lymphoma, acute lymphoblastic leukemia, or multiple myeloma. However, the current production method of CAR T cells is complex and time-consuming, especially for the autologous treatment where cell samples are shipped back and forth between the treatment site and cell production facilities. There exists a need for a method and apparatus to reduce cost and time in the production of CAR T cells, especially for the autologous treatment.

SUMMARY OF THE INVENTION

The present invention is directed to a method that satisfies this need. A method having features of the present invention for producing a population of T cells that express a chimeric antigen receptor (CAR) comprising the steps of providing a fluid sample including a population of T cells; labeling the population of T cells with magnetic beads; extracting the population of T cells from the fluid sample by flowing the fluid sample through a magnetic separator device; transducing the population of T cells to express a chimeric antigen receptor (CAR) by contacting the population of T cells with a vector that carries a CAR construct; and harvesting the population of T cells by flowing the solution through the magnetic separator device or another magnetic separator device. The method may further comprise the step of activating the population of T cells prior to the step of transducing the population of T cells.

According to another aspect of the present invention, a method for producing a population of T cells that express a chimeric antigen receptor (CAR) comprising the steps of providing a fluid sample including a population of T cells; labeling the population of T cells with magnetic beads; extracting the population of T cells from the fluid sample by flowing the fluid sample through a first conduit that passes through a first magnetic separator device; transducing the population of T cells to express a chimeric antigen receptor (CAR) by contacting the population of T cells with a population of lentivirus in a solution contained in an incubation container; and harvesting the population of T cells by flowing the solution through a second conduit that passes through a second magnetic separator device, wherein the first conduit, the incubation container, and the second conduit are fluidically connected by a network of fluidic lines. The first conduit, the incubation container, the second conduit, and the network of fluidic lines are components of a closed fluidic system. The method may further comprise the step of activating the population of T cells prior to the step of transducing the population of T cells.

According to still another aspect of the present invention, a method for producing a population of T cells that express a chimeric antigen receptor (CAR) comprising the steps of providing a fluid sample including a population of T cells; labeling the population of T cells with magnetic beads; extracting the population of T cells from the fluid sample by flowing the fluid sample through a conduit that passes through a magnetic separator device, transducing the population of T cells to express a chimeric antigen receptor (CAR) by contacting the population of T cells with a population of lentivirus in a solution contained in an incubation container; harvesting the population of T cells by flowing the solution through an acoustic separator device, wherein the conduit, the incubation container, and the acoustic separator device are fluidically connected by a network of fluidic lines. The conduit, the incubation container, the acoustic separator device, and the network of fluidic lines are components of a closed fluidic system. The method may further comprise the step of activating the population of T cells prior to the step of transducing the population of T cells.

According to yet another aspect of the present invention, a method for producing a population of T cells that express a chimeric antigen receptor (CAR) comprising the steps of providing a fluid sample including a population of T cells and other cells; labeling the other cells with magnetic beads; removing the other cells from the fluid sample by flowing the fluid sample through a conduit that passes through a magnetic separator device, transducing the population of T cells to express a chimeric antigen receptor (CAR) by contacting the population of T cells with a population of lentivirus in a solution contained in an incubation container; harvesting the population of T cells by flowing the solution through an acoustic separator device, wherein the conduit, the incubation container, and the acoustic separator device are fluidically connected by a network of fluidic lines. The conduit, the incubation container, the acoustic separator device, and the network of fluidic lines are components of a closed fluidic system. The method may further comprise the step of activating the population of T cells prior to the step of transducing the population of T cells.

According to still yet another aspect of the present invention, a method for producing a population of T cells that express a chimeric antigen receptor (CAR) comprising the steps of providing a fluid sample including a population of T cells; labeling the population of T cells with magnetic beads; extracting the population of T cells from the fluid sample by flowing the fluid sample through a first conduit that passes through a first magnetic separator device, transducing the population of T cells to express a chimeric antigen receptor (CAR) by contacting the population of T cells with a population of lentivirus and removing the magnetic beads from surfaces of T cells in a solution contained in an incubation container; removing the magnetic beads from the solution by flowing the solution through a second conduit that passes through a second magnetic separator device; harvesting the population of T cells by flowing the solution through an acoustic separator device, wherein the first conduit, the incubation container, the second conduit, and the acoustic separator device are fluidically connected by a network of fluidic lines. The first conduit, the incubation container, the second conduit, the acoustic separator device, and the network of fluidic lines are components of a closed fluidic system. The method may further comprise the step of activating the population of T cells prior to the step of transducing the population of T cells.

BRIEF DESCRIPTION OF DRAWINGS

These and other features, aspects, and advantages of the present invention will become better understood with regard to the following description, appended claims, and accompanying drawings where:

For purposes of clarity and brevity, like elements and components will bear the same designations and numbering throughout the Figures, which are not necessarily drawn to scale.

DETAILED DESCRIPTION OF THE INVENTION

Figure 1:
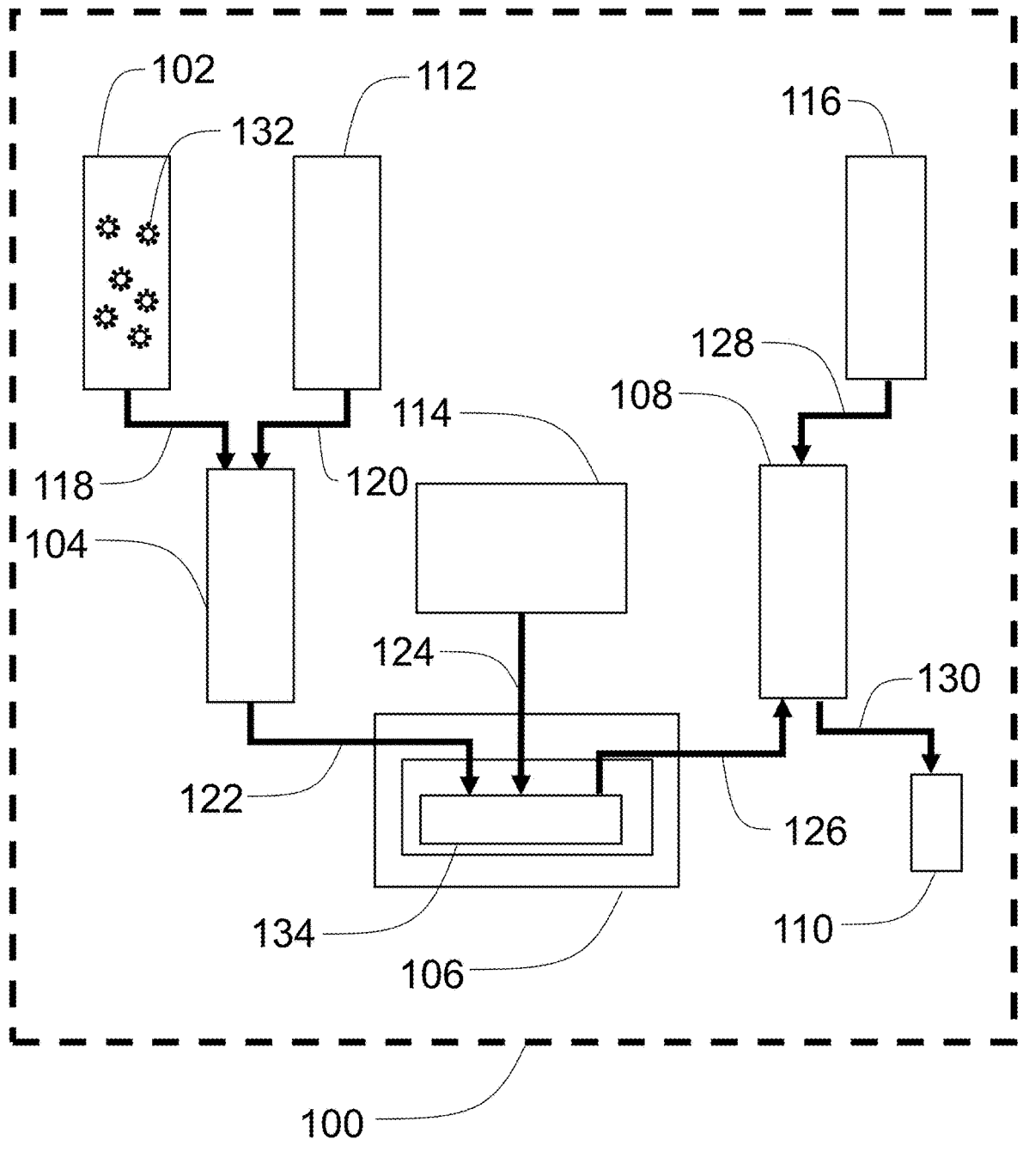
FIG. 1 is a block diagram showing an integrated system and components thereof that may be used for producing CAR T cells in accordance with a first embodiment of the present invention.

In the Summary above and in the Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously, except where the context excludes that possibility, and the method can include one or more other steps which are carried out before any of the defined steps, between two of the defined steps, or after all the defined steps, except where the context excludes that possibility.

The term "biological objects" as used herein includes cells, bacteria, viruses, molecules, particles including RNA and DNA, cell cluster, bacteria cluster, molecule cluster, and particle cluster.

The term "biological sample" as used herein includes blood, body fluid, tissue extracted from any part of the body, bone marrow, hair, nail, bone, tooth, liquid and solid from bodily discharge, or surface swab from any part of body. "Fluid sample," or "sample fluid," or "liquid sample," or "sample solution" may include a biological sample in its original liquid form, biological objects being dissolved or dispersed in a buffer fluid, or a biological sample dissociated from its original non-liquid form and dispersed in a buffer fluid. A buffer fluid is a liquid into which biological objects may be dissolved or dispersed without introducing contaminants or unwanted biological objects. Biological objects and biological sample may be obtained from human or animal. Biological objects may also be obtained from plants and environment including air, water, and soil. A fluid sample may contain various types of magnetic or optical labels, or one or more chemical reagents that may be added during various process steps.

The term "sample flow rate" or "flow rate" is used herein to describe the volume amount of a fluid flowing through a cross section of a channel, a conduit, a fluidic part, a fluidic path, or a fluidic line in a unit time.

In the art of cell sorting and enrichment, the target population of biological objects is referred to as the "specific" objects of interest and those biological objects that are isolated, but are not desired, are termed "non-specific." The term "purity" describes the frequency of target or specific biological objects of interest and is quantified by the number of target biological objects divided by the total number of biological objects expressed in percentage. The term "recovery ratio" or "recovery rate" describes the sorting efficiency of biological objects and is quantified by the number of target biological objects recovered after sorting divided by the number of target biological objects present in the initial sample expressed in percentage.

The term "at least" followed by a number is used herein to denote the start of a range beginning with that number, which may be a range having an upper limit or no upper limit, depending on the variable being defined. For example, "at least 1" means 1 or more than 1. The term "at most" followed by a number is used herein to denote the end of a range ending with that number, which may be a range having 1 or 0 as its lower limit, or a range having no lower limit, depending upon the variable being defined. For example, "at most 4" means 4 or less than 4, and "at most 40%" means 40% or less than 40%. When, in this specification, a range is given as "a first number to a second number" or "a first number–a second number," this means a range whose lower limit is the first number and whose upper limit is the second number. For example, "25 to 100 nm" means a range whose lower limit is 25 nm and whose upper limit is 100 nm.

Directional terms, such as "front," "back," "top," "bottom," and the like, may be used with reference to the orientation of the illustrated figure. Spatially relative terms, such as "beneath," "below," "under," "lower," "upper," "above," etc., may be used herein to describe one element's relationship to another element(s) as illustrated in the figure. Since articles and elements can be positioned in a number of different orientations, these terms are intended for illustration purposes and in no way limit the invention, except where the context excludes that possibility.

Where reference is made herein to a material AB composed of element A and element B, the material AB can be an alloy, a compound, or a combination thereof, except where the context excludes that possibility.

Provided herein are production apparatus and methods for manufacturing CAR T cells.

Embodiment 1: Positive Magnetic Selection and Positive Magnetic Purification This embodiment uses a first magnetic separator device to isolate or extract magnetically labeled target cells from initial sample for genetic modification, which may take place in a cell incubator, and then uses a second magnetic separator device to purify the genetically modified target cells.

FIG. 1 is a block diagram showing an integrated system 100 and components thereof that may be used for producing CAR T cells. The integrated system 100, which has control electronics, user interface, hardware, software, and firmware (not shown), includes a first container or bag 102 for holding a sample containing target cells for processing, a first magnetic separator device 104, a cell incubation chamber 106, a second magnetic separator device 108, a second container or bag 112 containing a buffer or solution for eluting the target cells from the first magnetic separator device 104, an incubation ingredient bank 114, a third container or bag 116 containing a buffer or solution for eluting the target cells from the second magnetic separator device 108, a fourth container or bag 110 for receiving the final cell product, and multiple fluidic lines 118-130 that provide fluidic interconnection between individual components in the integrated system 100.

The first container or bag 102 holds a fluid sample that includes target cells 132 (e.g., T cells) with magnetic labels attached thereto. The fluid sample may contain whole blood, leukopak, PBMC, and/or other leukapheresis products containing the target cells with magnetic labels attached thereto. The magnetic labels may be attached to the target cells during an incubation process taking place in the same first container or bag 102.

The first magnetic separator device 104, which is connected to the first container or bag 102 through the fluidic line 118, is used to extract the magnetically labeled target cells from the fluid sample.

The second container or bag 112, which is connected to an inlet of the first magnetic separator device 104 through the fluidic line 120, contains the buffer or solution for eluting the magnetically labeled target cells remained in the first magnetic separator device 104 after the passage of the fluid sample. The buffer or solution in the second container or bag 112 may contain PBS based solution, culture media based solution, human serum, glucose, or any combination thereof.

The cell incubation chamber 106 may be used for cell genomic engineering, cell modification, cell transduction, or cell transfection. The cell incubation chamber 106 includes a cell container 134 therein that is connected to an outlet of the first magnetic separator device 104 through the fluidic line 122. The cell container 134 contains the magnetically labeled target cells, the buffer or solution for eluting the cells from the first magnetic separator device 104, and optionally one or more buffers or solutions from the incubation ingredient bank 114 connected to the cell container 134 through the fluidic line 124. The cell incubation chamber 106 may have one or more gas lines (e.g., $CO_2$) (not shown) connected thereto for providing an environment with desired gas composition (e.g., 5.0%±0.1% $CO_2$). The cell incubation chamber 106 may also have a heating and cooling mechanism (not shown) that can maintain the temperature constant (e.g., 37.0±0.1° C.) inside the chamber. Additionally, the cell incubation chamber 106 may also include an air circulation mechanism, such as a fan, to circulate air or other gas mixtures therein to make the temperature more uniform throughout the chamber 106. The cell container 134 and content therein may be heated or cooled by convection through the surrounding environment in the cell incubation chamber 106. The cell container 134 may also have a porous or permeable portion, such as membrane and air vent, that allows gas molecules in the surrounding environment to diffuse for flow through, thereby exposing the content of the cell container 134 to air or other gas mixtures inside the cell incubation chamber 106.

The incubation ingredient tank 114 may include one or more of the following items: culture media, vectors for cell transduction or transfection, lentivirus for transduction, buffers or solutions for non-viral transfection.

The cell incubation chamber 106 may further include means that can induce the target cell membrane to open, such as but not limited to cell electroporation, mechanical cell deformation, temperature, ultrasound, and optical, thereby allowing genetic materials to enter the target cells from the surrounding media in the cell container 134. Genetic materials can also be introduced into the target cells using droplet based genetic material injection or penetration through the target cell membrane.

The cell incubation chamber 106 may provide the environment for the transduction process. For example, lentivirus or other viruses may be used to transfer genomic materials into the target T cells to induce chimeric antigen receptor (CAR) growth on the cell surface.

The second magnetic separator device 108, which is connected to the cell container 134 inside the cell incubation chamber 106 through the fluidic line 126, is used to extract the target cells that still retain magnetic labels on their surface from the mixture of solutions and/or media used in the cell container 134 after genetic modification by transduction or transfection.

The third container or bag 116, which is connected to an inlet of the second magnetic separator device 108 through the fluidic line 128, contains a buffer or solution for eluting the magnetically labeled target cells remained in the second magnetic separator device 108 after the passage of the fluid sample. The buffer or solution in the third container or bag 116 may contain PBS based solution, saline based solution, human serum, glucose, or any combination thereof.

The fourth container or bag 110, which is connected to an outlet of the second magnetic separator device 108 through the fluidic line 130, contains the genetically modified target cells (e.g., CAR T cells) in a solution that may be intravenously administered to patients.

The network of the fluidic lines 118-130, the containers or bags 102, 112, 116, 110, the cell container 134, and the conduits passing through the first and second magnetic separator devices 104 and 108 may be constructed, interconnected, and supplied as an integrated disposable set, which may be sterile and sealed from the surrounding environment.

With continued reference to FIG. 1, the process begins by providing the first container or bag 102 that includes therein a first fluid sample containing the magnetically labeled target cells 132 (e.g., T cells). For previously frozen samples, the first fluid sample may be prepared by first thawing the frozen samples and then extract the target cells and other biological objects, if any, from the thawed sample fluid by centrifugation. The resultant target cells and other biological objects, if any, are resuspended in a buffer fluid and filtered using a mesh size of between 15 and 100 μm. A reagent containing magnetic labels is added to the filtered buffer fluid containing the target cells, thereby forming the first fluid sample. Alternatively, the target cells may be magnetically labeled through an indirect process by first adding a reagent containing intermediate links that attach to the target cells prior to adding the reagent containing the magnetic labels that attach to the intermediate links.

The first fluid sample is flowed into the inlet of the first magnetic separator device 104 through the fluidic line 118 for the first magnetic sorting process. As the first fluid sample flows through the first magnetic separator device 104, the magnetically labeled target cells 132 are retained in the first magnetic separator device 104 by a magnetic field, while the depleted first fluid sample exit the first magnetic separator device 104 to a waste container or bag (not shown). After the first fluid sample completely passes through the first magnetic separator device 104, the magnetic field acting on the magnetically labeled target cells 132 is reduced or removed, and a first eluant, such as a buffer fluid, in the second container or bag 112 flows through the fluidic line 120 and into the first magnetic separator device 104 to elute the magnetically labeled target cells 132 into the cell container 134 via the fluidic line 122. Additionally, one or more solutions from the incubation ingredient tank 114, such as but not limited to culture media, vectors for cell transduction or transfection, lentivirus for transduction, buffers or solutions for non-viral transfection, are injected into the cell container 134 through the fluidic line 124 for modifying the genetic structure of the magnetically labeled target cells 132. The magnetically labeled target cells 132 (e.g., T cells) can be transduced to express a CAR by contacting the target cells with vectors that carry CAR constructs, including viral vectors, such as lentivirus and retrovirus, and non-viral vectors, such as plasmid, lipid nanoparticles, and mRNA.

The transduction or transfection process is carried out in the cell incubation chamber 106 while the magnetically labeled target cells 132 are immersed in a transduction or transfection media, which comprises the first eluant and the one or more solutions from the incubation ingredient tank 114. The temperature and gas composition inside the cell incubation chamber 106 can be controlled during the transduction or transfection process. For example, the temperature and gas composition inside the cell incubation chamber 106 may be maintained at 37.0±0.1° C. and 5.0%±0.1% $CO_2$, respectively, for a period of time ranging from 10 min to 72 hours while the genetic structure of the magnetically labeled target cells 132 is being modified in the cell container 134.

After the transduction or transfection process is completed, a buffer fluid for facilitating the subsequent magnetic sorting process may be added to the transduction or transfection media in the cell container 134 from the incubation ingredient tank 114. The mixture of the transduction or transfection media and the buffer fluid for facilitating the magnetic sorting process, if any, forms the second fluid sample containing the magnetically labeled target cells with modified genetic structure.

The second fluid sample is then flowed into the inlet of the second magnetic separator device 108 through the fluidic line 126 to extract the magnetically labeled target cells with modified genetic structure by the second magnetic sorting process. As the second fluid sample flows through the second magnetic separator device 108, the magnetically labeled target cells are retained in the second magnetic separator device 108 by a magnetic field, while the depleted second fluid sample exit the second magnetic separator device 108 to a waste container or bag (not shown). After the second fluid sample completely passes through the second magnetic separator device 108, the magnetic field acting on the magnetically labeled target cells is reduced or removed, and a second eluant, such as a buffer fluid, in the third container or bag 116 flows through the fluidic line 128 and into the second magnetic separator device 108 to elute the magnetically labeled target cells into the fourth container or bag 110 via the fluidic line 130. After the completion of the second magnetic sorting process, the fourth container or bag 110 containing the magnetically labeled target cells with modified genetic structure may be severed from the rest of the integrated system 100 without exposing its content to atmosphere. The content in the fourth container or bag 110 may be intravenously administered to patients.

Figure 2:
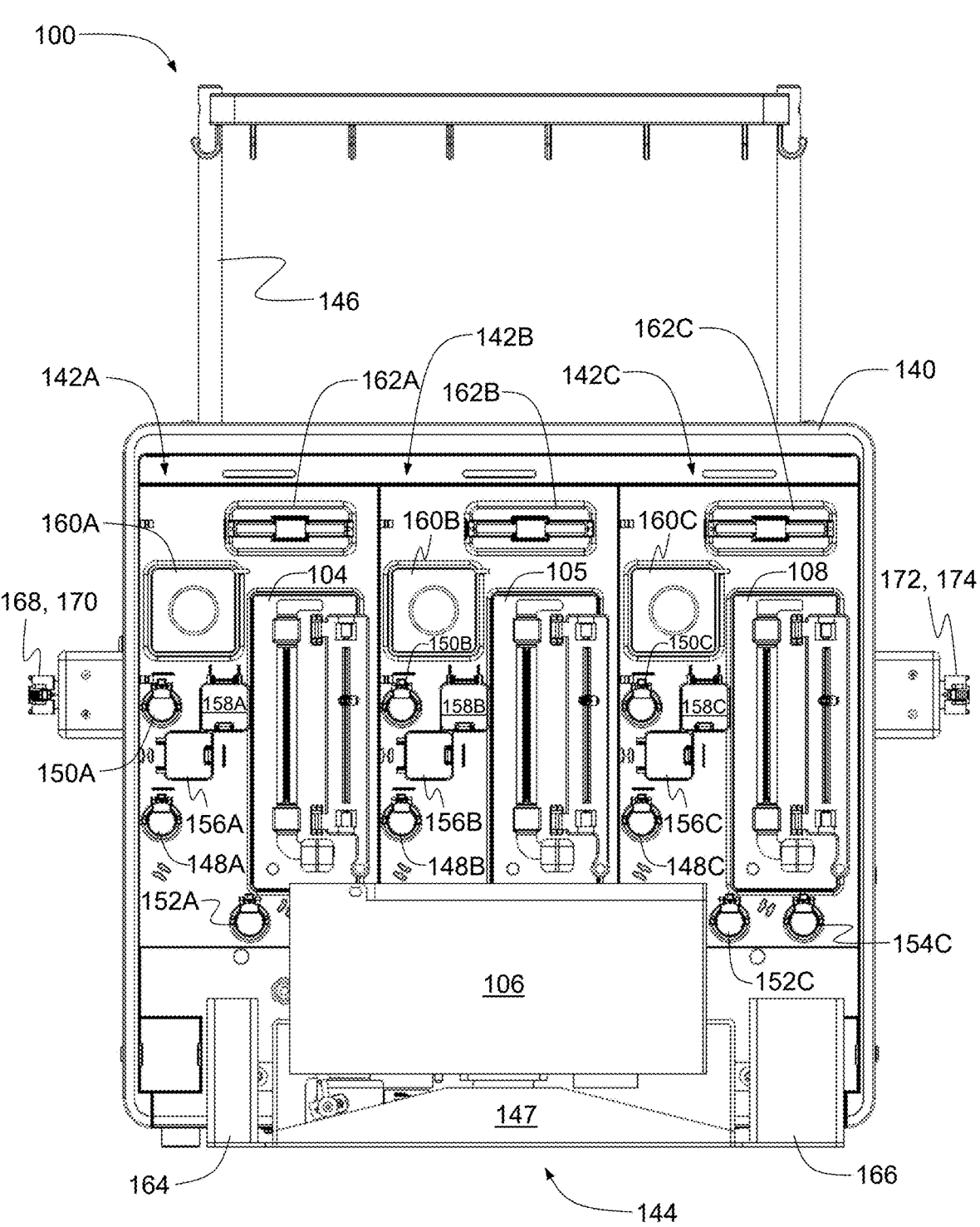
FIG. 2 is a frontal view of the integrated system that may be used to produce CAR T cells from whole blood or leukapheresis products in accordance with the first embodiment of the present invention.

FIG. 2 is a frontal view of the integrated system 100 that may be used to produce CAR T cells from whole blood or samples containing T cells (e.g., leukapheresis products) in accordance with the process described above. The system 100 may utilize a closed fluidic assembly to become a closed processing system that can be deployed in a facility that lacks a stringent sterile or clean environment, such as the treatment facility, thereby alleviating much of the common logistic issues encountered in the autologous treatment.

FIG. 2 shows the automated production system 100 including a shell or housing structure 140, first, second, and third magnetic separator modules 142A-142C residing in the housing structure 140, an incubation module 144, a sample rack 146 mounted on top of the housing structure 140, and first and second sample bag holders 164, 166. The fluidic lines and sample bags connected thereto, which may be supplied as an integrated disposable tubing set, and the computer used for controlling the system 100 are omitted in the drawing in order to present an unobstructive view of the magnetic separator modules 142A-142C.

The incubation module 144 includes an incubation chamber 106 sitting on top of a rocker base 147. Each of the magnetic separator modules 142A-142C includes a first pinch valve 148A, 148B, 148C, a second pinch valve 150A, 150B, 150C, a third pinch valve 152A, 152B, 152C, a fourth pinch valve 154A, 154B, 154C, a first air detector 156A, 156B, 156C, a second air detector 158A, 158B, 158C, a peristaltic pump 160A, 160B, 160C, a blockage sensor 162A, 162B, 162C, and a magnetic separator device 104, 105, 108.

The system 100 may also include additional pinch valves 168, 170 disposed on one side of the housing structure 140 and additional pinch valves 172, 174 disposed on the other side of the housing structure 140. The electromechanical components 104-108, 147, 148A/B/C-162A/B/C, 168-174 may be controlled or automated by a computer or microprocessor (not shown).

Figure 3:
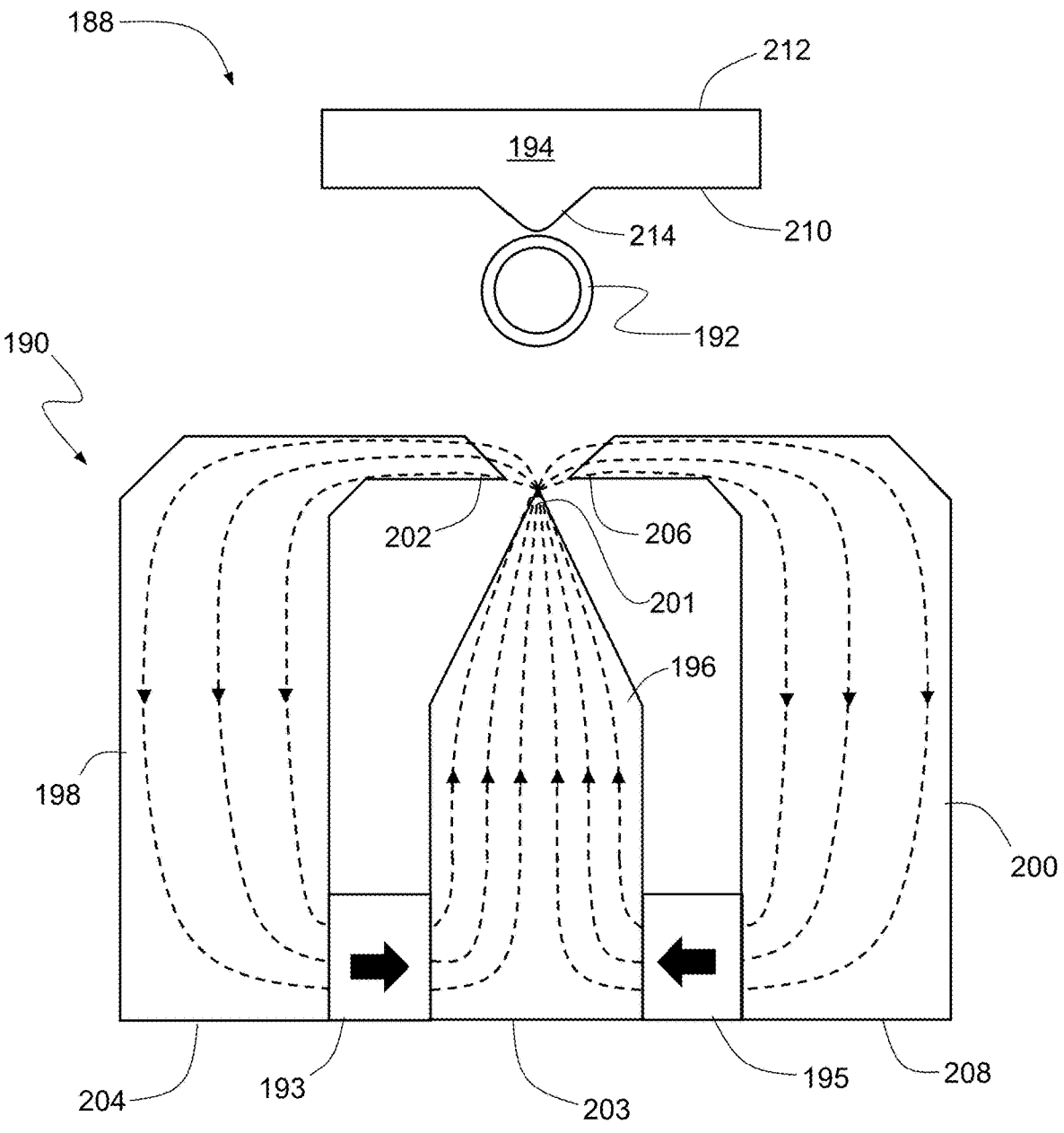
FIG. 3 is a cross-sectional view corresponding to a column-free magnetic separator device for sorting magnetically labeled cells flowing through a conduit when the holder and conduit are disengaged from the magnetic assembly.

Each of the magnetic separator devices 104, 105, 108 may have a structure that is identical or substantially similar to a magnetic separator device 188, the cross-sectional view of which is shown in FIG. 3. The magnetic separator device 188 includes a magnetic assembly 190 for generating a magnetic field, a conduit 192 made of a pliable and/or flexible material for flowing a fluid sample for sorting, and a holder 194 for supporting the conduit 192. The figure shows the conduit 192 and the holder 194 being disengaged from the magnetic assembly 190. During the magnetic sorting process, however, the conduit 192 would be placed in close proximity to the magnetic assembly 190, thereby exposing the conduit 192 to the magnetic field generated by the magnetic assembly 190.

The magnetic assembly 190 for generating the magnetic field to attract the magnetically labeled biological objects in the conduit 192 includes a magnetic flux source, which comprises first and second permanent magnets 193 and 195, a center magnetic flux guide 196 for conducting the magnetic flux from the magnetic flux source and forming a magnetic field, first and second side magnetic flux guides 198 and 200 disposed on opposite sides of the center magnetic flux guide 196 for conducting the magnetic flux from the magnetic flux source and forming the magnetic field at the gap between the flux guides 196-200.

The center magnetic flux guide 196 has a center tip 201 with a tapering shape and a center base 203 physically and/or magnetically coupled to the first and second permanent magnets 193 and 195 at their first pole (e.g., North pole). The center tip 201 may have a smaller cross section, which may be defined herein as the cross-sectional area perpendicular to the magnetic flux flow, than the center base 203, thereby concentrating the magnetic flux from the center base 203 to the center tip 201. The first side magnetic flux guide 198 has a first side tip 202 and a first side base 204 physically and/or magnetically coupled to the first permanent magnet 193 at its second pole (e.g., South pole). The first side tip 202 may have a smaller cross section than the first side base 204, thereby concentrating the magnetic flux from the first side base 204 to the first side tip 202. The second side magnetic flux guide 200 has a second side tip 206 and a second side base 208 physically and/or magnetically coupled to the second permanent magnet 195 at its second pole (e.g., South pole). The second side tip 206 may have a smaller cross section than the second side base 208, thereby concentrating the magnetic flux from the second side base 208 to the second side tip 206. Accordingly, each of the tips 201, 202, and 206 may have a higher magnetic flux density than the corresponding base 203, 204, or 208. The first and second side magnetic flux guides 198 and 200 may be parallel at their bases 204 and 208 and bending or kinking inward toward the center tip 201 at their tips 202 and 206, which may be pointed at each other. The ends of the first and second side tips 202 and 206 may each have a chisel edge profile with the bevel side facing upward or outward away from the center magnetic flux guide 196. The center tip 201 may be positioned below the first and second side tips 202 and 206. The conduit 192 may be operably nestled in the gap or concave space delineated by the tip end of the center tip 201 and the bevels of the first and second side tips 202 and 206 during the magnetic sorting process, thereby exposing the conduit 192 to the magnetic field generated by the magnetic assembly 190.

The first permanent magnet 193 may be disposed between the center base 203 and the first side base 204, and the second permanent magnet 195 may be disposed between the center base 203 and the second side base 208. The first and second permanent magnets 193 and 195 have opposite magnetization directions that may be oriented substantially perpendicular to the center magnetic flux guide 196.

The center base 203 is magnetically coupled to the first and second permanent magnets 193 and 195 at their first pole (e.g., North pole), while the first and second side bases 204 and 208 are magnetically coupled to the first and second permanent magnets 193 and 195 at their second pole (e.g., South pole), respectively, thereby rendering the first and second side tips 202 and 206 (second polarity) and the center tip 201 (first polarity) to have opposite magnetic polarities and forming a strong magnetic field at or near the gaps between the tips 201, 202, and 206 to deposit the magnetically labeled biological objects on the conduit wall.

With continuing reference to FIG. 3, the holder 194 may have a first surface 210 facing the conduit 192 and a second surface 212 opposite the first surface 210. The first surface 210 may have a ridge structure 214 protruded from the first surface 210 that functions as a mechanical press for pushing the conduit 192 into the gap or concave space delineated by the tip end of the center tip 201 and the bevels of the first and second side tips 202 and 206 during the magnetic sorting process. Additionally, the ridge structure 214 of the holder 194 may be made of a magnetic material that conducts magnetic flux like a "floating" or top magnetic flux guide. In addition to acting like a mechanical press for pushing the conduit 192 against the tips 201, 202, and 206, the ridge structure 214 made of the magnetic material may magnetically interact with the tips 201, 202, and 206 to further enhance the magnetic field therebetween, thereby increasing the magnetic sorting efficiency.

Figure 4:
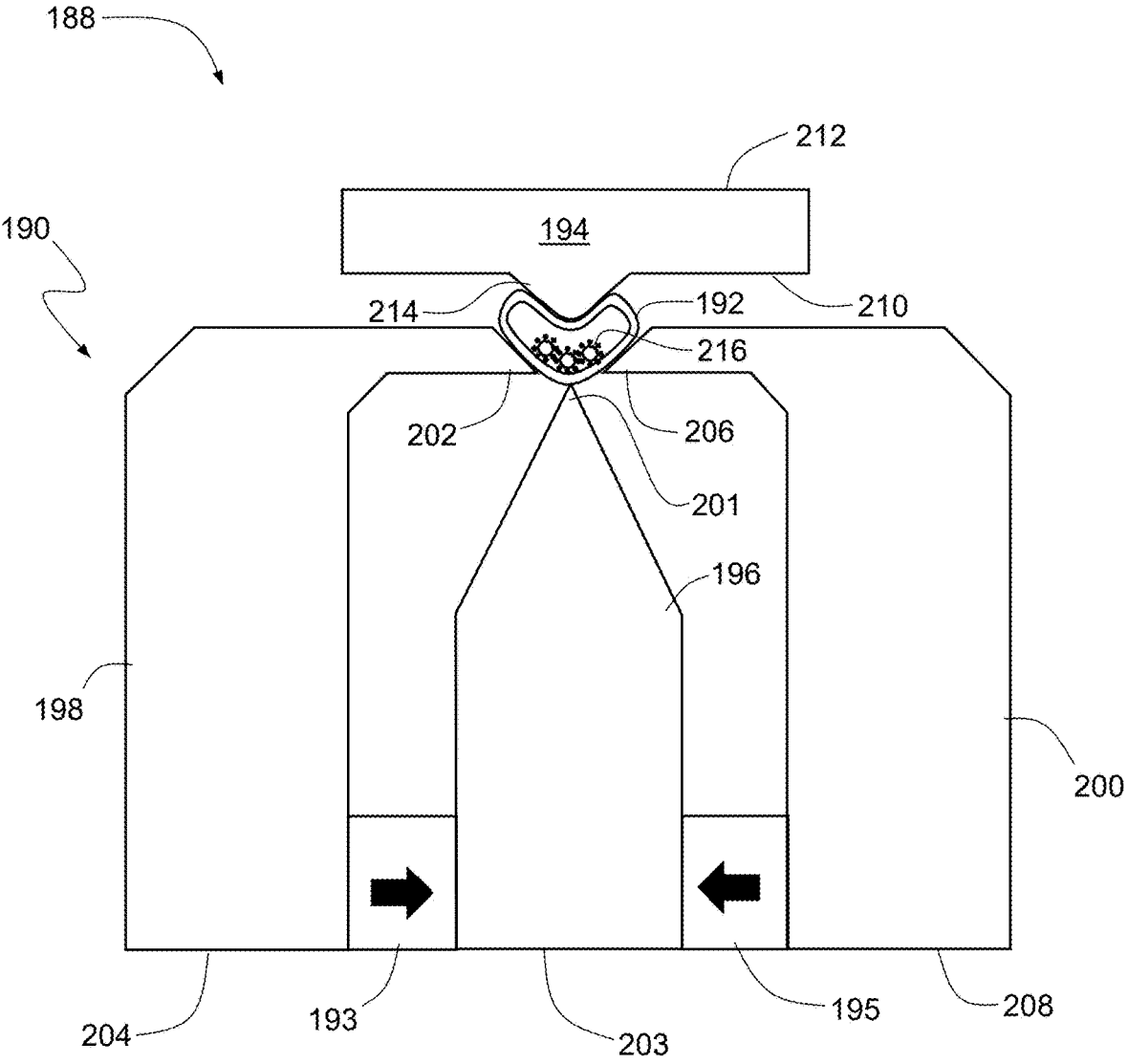
FIG. 4 is a cross-sectional view of the magnetic separator device of FIG. 3 when the conduit is squeezed against the tips of the magnetic assembly by the holder during the magnetic sorting process.

FIG. 4 is a cross-sectional view of the magnetic separator device 188 when the conduit 192 is squeezed between the ridge structure 214 of the holder 194 and the tip ends 201, 202, and 206 of the three magnetic flux guides 196-200 during the magnetic sorting process. The holder 194 may push the deformed or distorted conduit 192 further into the gap between the center tip 201 and the first side tip 202 and the gap between the center tip 201 and the second side tip

206, where the magnetic field may be the strongest. Pushing the conduit 192 against the tip end of the center tip 201 and the bevels of the first and second side tips 202 and 206 may expose more fluid sample flowing through the conduit 192 to stronger magnetic field. During the magnetic sorting process, the magnetically labeled biological objects 216 may be deposited on the bottom of the conduit 192 near the center tip 201, where the magnetic field gradient may be highest.

In the embodiment where the ridge structure 214 is made of a soft magnetic material, the ridge structure 214 may act like a top magnetic flux guide when positioned in close proximity to the tips 201, 202, and 206 during the magnetic sorting process. The magnetic ridge structure 214 may conduct flux from the first and second side magnetic flux guides 198 and 200 and thus may have the same magnetic polarity (second polarity) as the first and second side tips 202 and 206, thereby further enhancing the magnetic field between the ridge structure 214 and the center tip 201.

The magnetic flux guides 196-200 each may be made of a soft magnetic material or a material with relatively high magnetic permeability that comprises any one of iron (Fe), cobalt (Co), nickel (Ni), or any combination thereof. For example and without limitation, any of the magnetic flux guides 196-200 may be made of iron. The conduit 192 may be made of any suitable flexible and/or pliable material that may be bent or deformed, such as but not limited to rubber, plastics, or any suitable polymeric material. The holder 194 may be made of any suitable nonmagnetic material, such as but not limited to aluminum, glass, a nonferrous metal or alloy, plastics, or any suitable polymeric material. In some embodiments, the ridge structure 214 of the holder 194 that comes into contact with the conduit 192 may be made of a soft magnetic material, such as but not limited to any of the soft magnetic materials described above for the magnetic flux guides 196-200.

Operation of the magnetic separator device 188, including the recovery of the magnetically labeled target cells, is described more fully in U.S. patent application Ser. No. 18/795,047, which is incorporated herein by reference in its entirety. Other magnetic flux sources and column-free magnetic separator devices, such as those disclosed in U.S. application Ser. No. 18/072,362, which is incorporated herein by reference, may also be used to separate the magnetically labeled target cells from the fluid sample.

Referring back to FIG. 2, the incubation module 144 includes the cell incubation chamber 106 sitting atop of the rocker base 147. The incubation chamber 106 has a heater that can uniformly maintain the temperature inside the chamber 106 between room temperature and 50° C. The $CO_2$ concentration inside the chamber 106 can be varied between 0 and 10% to provide an optimal environment for cells. The rocker base 147 may move the chamber 106 at a speed between 2 rpm and 4 rpm. The swaying motion of the chamber 106 caused by the rocker base 147 may facilitate uniform mixing of the fluid content inside the cell container 134. The rocker base 147 may remain stationary during cell activation, transduction, or expansion process. After the incubation process, the rocker base 147 may effectuate the cell container 134 inside the chamber 106 to sway, causing the fluid in the cell container 134 to rinse cells off the surface of the cell container 134. The rocker base 147 may also be used to facilitate draining of the cell container 134 by tilting the incubation chamber 106 to a fixed position to allow the end of the outlet tube to reach the bottom of the fluid inside the cell container 134.

The system 100 has a modular design comprising three magnetic separator modules 142A-142C and one incubation module 144. The modules 142A-142C, 144 may be fluidically connected in series, parallel, or a combination thereof by a closed fluidic assembly that includes sample bags, cell containers, and all fluidic lines including conduits passing through the magnetic separator devices.

Figure 5:
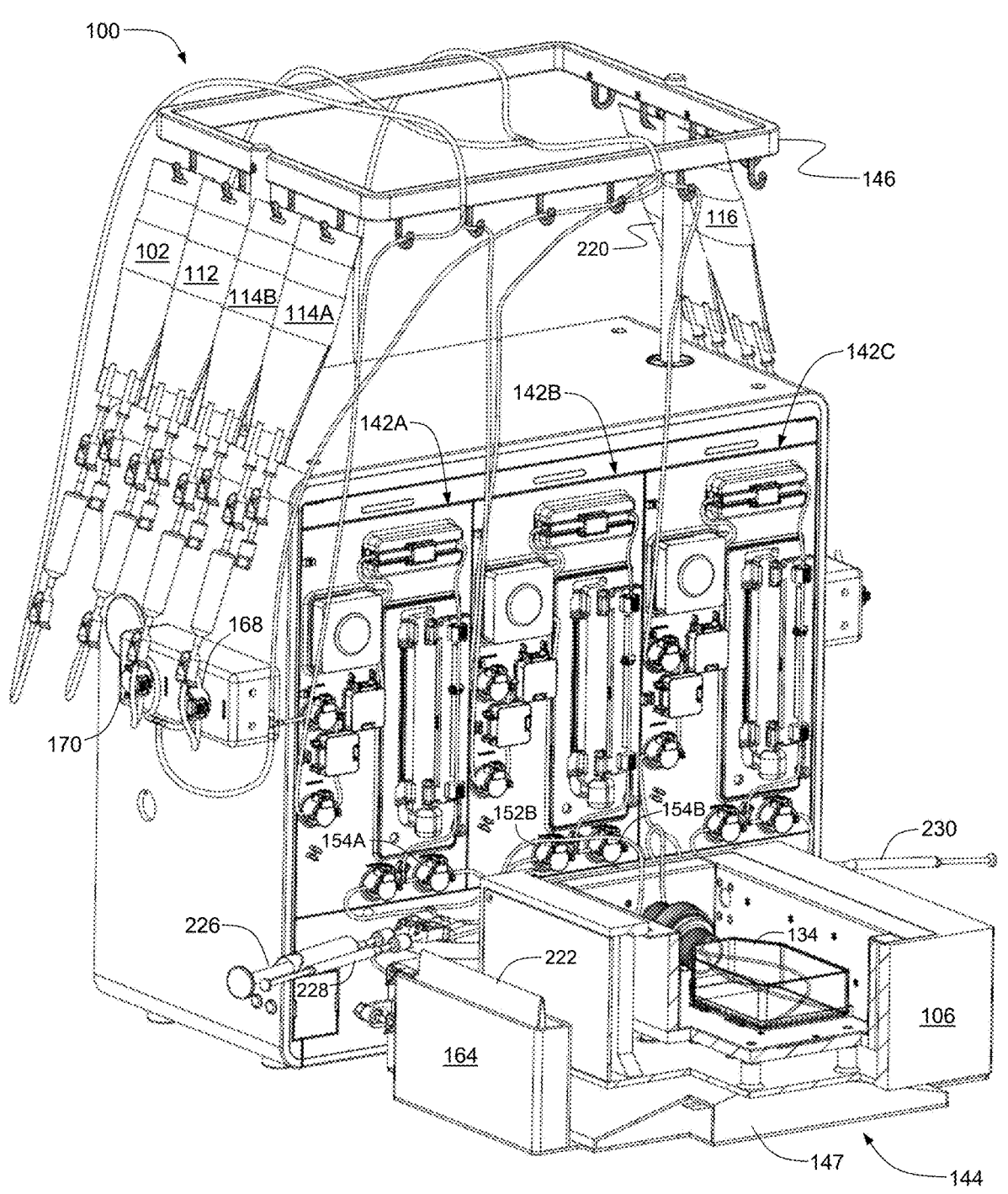
FIG. 5 is a perspective view of the integrated system of FIG. 2 using a closed fluidic assembly in the form of an integrated tubing set for manufacturing CAR T cells in accordance with the first embodiment of the present invention.
Figure 6:
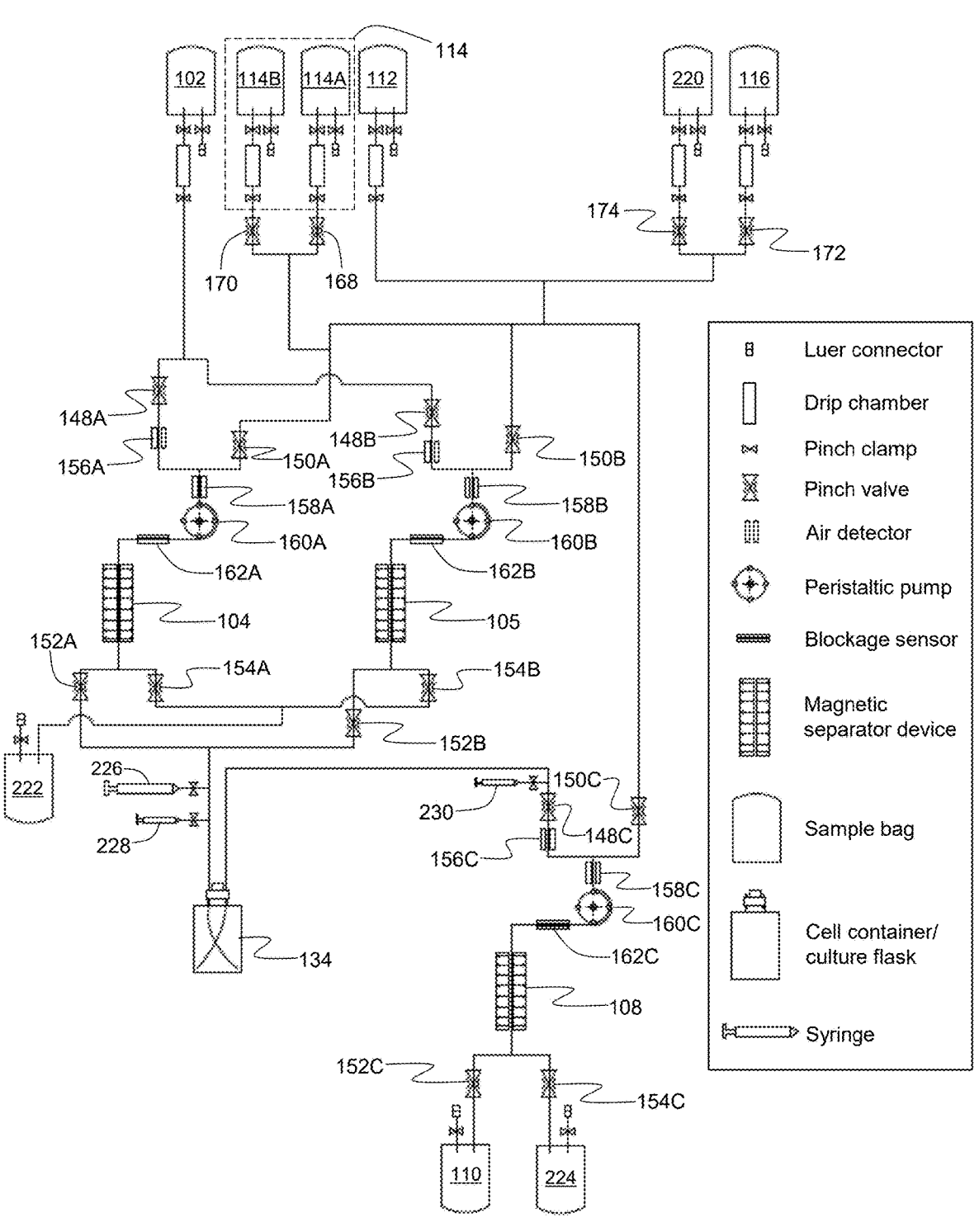
FIG. 6 is fluidic circuit diagram corresponding to the integrated system of FIG. 5.

FIG. 5 is a perspective view of the system 100 using a closed fluidic assembly in the form of an integrated tubing set for manufacturing CAR T cells. For reasons of legibility, electromechanical components labeled in FIG. 2 are not relabeled in the drawing to clearly show the routing of fluidic lines. The perspective view also shows the pinch valves 152B, 154A, 154B that are previously blocked by the cell incubation chamber 106 and the pinch valves 168, 170 disposed on one side of the housing structure 140 in the frontal view of FIG. 2. The lid and a section of the side wall of the incubation chamber 106 are further removed to expose the cell container 134 in the form of a common cell culture flask inside the chamber 106. The cap of the cell culture flask 134 contains an air filter that is vented to the environment inside the incubation chamber 106 while preserving sterility inside the flask 134. FIG. 6 is a fluidic circuit diagram corresponding to the system 100 shown in FIG. 5.

Referring to FIGS. 2, 5, and 6, the fluidic assembly of the system 100 is arranged to use the first and third magnetic separator devices 104, 105 that are fluidically coupled in parallel to extract the magnetically labeled target cells (e.g., T cells) from the first fluid sample in the first magnetic sorting process and the second magnetic separator device 108 for the subsequent second magnetic sorting process. The use of two magnetic separator devices 104, 105 for the first magnetic sorting process enables the system 100 to increase the sorting throughput and accommodate a larger volume of the first fluid sample, such as whole blood.

The first, second, third, and fourth containers or bags 102, 112, 116, 110 are in the form of sample bags. The sample bags 102 and 112 are both fluidically connected to the inlets of the first and third magnetic separator devices 104, 105. In addition to the sample bag 116, another sample bag 220, which may also contain cryopreservation solution, storage media, PBS based solution, saline based solution, human serum, glucose, or any combination thereof, is also fluidically connected to the inlet of the second magnetic separator device 108. The incubation ingredient bank 114 includes at least two sample bags 114A, 114B fluidically connected to the cell container 134 through the magnetic separator devices 104, 105. Each of the sample bags 114A, 114B may include culture media, vectors for cell transduction or transfection, lentivirus for transduction, buffers or solutions for non-viral transfection, or cell activation reagent. Prior to the transduction or transfection process, the target T cells in the cell container 134 may be activated by flowing a cell activation reagent (e.g., solution CD3/CD28 magnetic beads) from one of the sample bags 114A, 114B into the cell container 134.

The fluidic assembly of the system 100 further includes a sample bag 222 fluidically connected to the outlets of the first and third magnetic separator devices 104, 105 for collecting waste from the devices 104, 105, and another sample bag 224 fluidically connected to the outlet of the second magnetic separator device 108 for collecting waste from the device 108. The sample bag 222 for collecting waste from the first and third magnetic separator devices 104, 105 may be placed in the first bag holder 164. The sample bags 110, 224 for respectively collecting the final cell product and waste from the second magnetic separator device 108 may be placed in the second bag holder 166. All other sample bags 102, 112, 114A, 114B, 116, 220, which provide materials for the manufacturing process, may be hung on the sample rack 146. The fluidic assembly of the system 100 may include additional sample bags for various purposes. Each of the sample bags 102, 110, 112, 114A, 114B, 116, 220-224 may have an inlet port with a Luer connector connected thereto and an outlet port with a drip chamber connected thereto. Additionally, the fluid flowing through the inlet and outlet ports of each sample bag may be controlled or regulated by one or more manual pinch clamps attached thereto.

The fluidic assembly of the system 100 may also include syringes 226, 228, 230. The syringes 226, 228, which may be fluidically connected to the inlet of the cell container 134, may be used to extract a sample of the magnetically separated target cells after the first magnetic sorting process or may inject culture media, vectors for cell transduction or transfection, lentivirus for transduction, buffers or solutions for non-viral transfection, or cell activation reagent into the cell container 134. The syringe 230, which may be fluidically connected to the outlet of the cell container 134, may be used to extract a sample of the genetically modified target cells after the transduction or transfection process is completed.

With continued reference to FIG. 6, the fluidic circuit corresponding to the system 100 includes the sample bags 102, 110, 112, 114A, 114B, 116, 220-224, the syringes 226-230, and the cell container 134, all interconnected by a network of fluidic lines that pass through the electromechanical components, such as the pinch valves 148A-148C, 150A-150C, 152A-152C, 154A-154C, 168-172, the air detectors 156A-156C, 158A-158C, the blockage sensors 162A-162C, the peristaltic pumps 160A-160C, and the magnetic separator devices 104, 105, 108. The sample bags 102, 110, 112, 114A, 114B, 116, 220-224, the syringes 226-230, the cell container 134, and the network of fluidic lines including the conduits passing through the magnetic separator devices 104, 105, 108 may be constructed, interconnected, sterilized, and supplied as an integrated disposable set. The electromechanical components of the system 100 are external to the tubing set and therefore do not come into contact the fluid in the tubing set.

The first container or sample bag 102, which may contain target cells for processing, is fluidically connected to the inlet of the conduit passing through the first magnetic separator device 104 by one or more fluidic lines that pass through the first pinch valve 148A, the first air detector 156A, the second air detector 158A, the peristaltic pump 160A, and the blockage sensor 162A, and is also fluidically connected to the inlet of the conduit passing through the third magnetic separator device 105 by one or more fluidic lines that pass through the first pinch valve 148B, the first air detector 156B, the second air detector 158B, the peristaltic pump 160B, and the blockage sensor 162B. The second container or sample bag 112, which may contain a buffer solution or culture media, is fluidically connected to the inlet of the conduit passing through the first magnetic separator device 104 by one or more fluidic lines that pass through the second pinch valve 150A, the second air detector 158A, the peristaltic pump 160A, and the blockage sensor 162A, and is also fluidically connected to the inlet of the conduit passing through the third magnetic separator device 105 through one or more fluidic lines that pass through the second pinch valve 150B, the second air detector 158B, the peristaltic pump 160B, and the blockage sensor 162B.

The inlet of the cell container 134 is fluidically connected to the outlet of the conduit passing through the first magnetic separator device 104 by one or more fluidic lines that pass through the third pinch valve 152A, and is also fluidically connected to the outlet of the conduit passing through the third magnetic separator device 105 by one or more fluidic lines that pass through the third pinch valve 152B. The syringes 226, 228 may be fluidically connected to a fluidic line between the inlet of the cell container 134 and the third pinch valves 152A, 152B. The sample bag 222, which may store waste fluid such as sample fluid after target cell extraction, is fluidically connected to the outlet of the conduit passing through the first magnetic separator device 104 by one or more fluidic lines that pass through the fourth pinch valve 154A, and is also fluidically connected to the outlet of the conduit passing through the third magnetic separator device 105 by one or more fluidic lines that pass through the fourth pinch valve 154B.

The outlet of the cell container 134 is fluidically connected to the inlet of the conduit passing through the second magnetic separator device 108 by one or more fluidic lines that pass through the first pinch valve 148C, the first air detector 156C, the second air detector 158C, the peristaltic pump 160C, and the blockage sensor 162C. The syringe 230 may be fluidically connected to a fluidic line connected to the outlet of the cell container 134. The third container or sample bag 116 is fluidically connected to the inlet of the conduit passing through the second magnetic separator device 108 by one or more fluidic lines that pass through the pinch valve 172, the second pinch valve 150C, the second air detector 158C, the peristaltic pump 160C, and the blockage sensor 162C. The sample bag 220 is fluidically connected to the inlet of the conduit passing through the second magnetic separator device 108 by one or more fluidic lines that pass through the pinch valve 174, the second pinch valve 150C, the second air detector 158C, the peristaltic pump 160C, and the blockage sensor 162C.

The outlet of the conduit passing through the second magnetic separator device 108 is fluidically connected to the fourth container or sample bag 110 by one or more fluidic lines that pass through the third pinch valve 152C, and is also fluidically connected to the sample bag 224, which may be used to receive waste fluid, by one or more fluidic lines that pass through the fourth pinch valve 154C.

The sample bag 114A of the incubation ingredient bank 114 is fluidically connected to the inlet of the cell container 134 by one or more fluidic lines that pass through the pinch valve 168, the second pinch valve 150A, the second air detector 158A, the peristaltic pump 160A, the blockage sensor 162A, the first magnetic separator device 104, and the third pinch valve 152A, and by one or more fluidic lines that pass through the pinch valve 168, the second pinch valve 150B, the second air detector 158B, the peristaltic pump 160B, the blockage sensor 162B, the third magnetic separator device 105, and the third pinch valve 152B. Similarly, the sample bag 114B of the incubation ingredient bank 114 is fluidically connected to the inlet of the cell container 134 by one or more fluidic lines that pass through the pinch valve 170, the second pinch valve 150A, the second air detector 158A, the peristaltic pump 160A, the blockage sensor 162A, the first magnetic separator device 104, and the third pinch valve 152A, and by one or more fluidic lines that pass through the pinch valve 170, the second pinch valve 150B, the second air detector 158B, the peristaltic pump 160B, the blockage sensor 162B, the third magnetic separator device 105, and the third pinch valve 152B.

Embodiment 2: Positive Magnetic Selection and Acoustic Purification

This embodiment uses a magnetic separator device to isolate or extract magnetically labeled target cells for genetic modification, which may take place in a cell incubator, and then uses an acoustic separator device to purify the genetically modified target cells.

Figure 7:
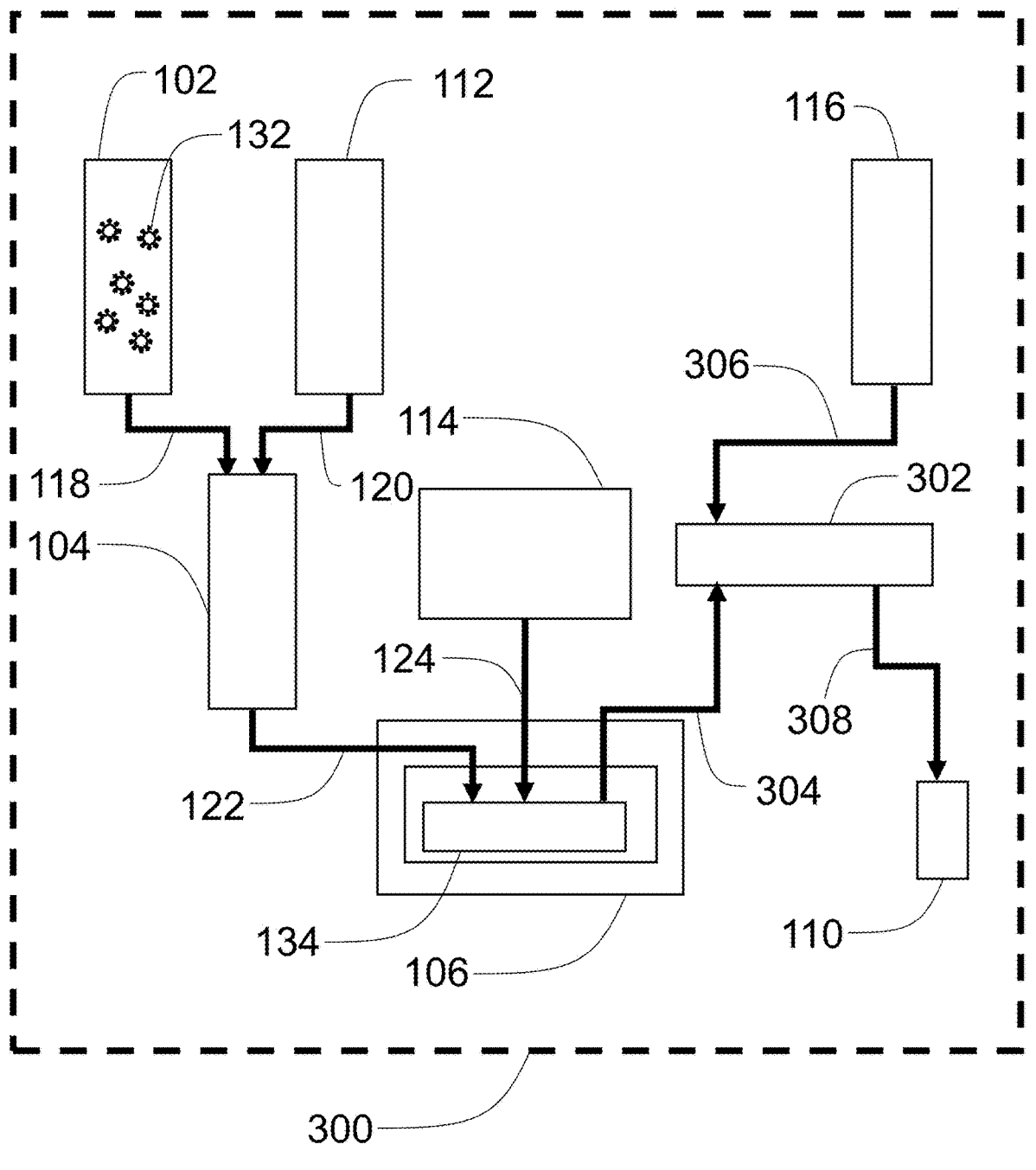
FIG. 7 is a block diagram showing another integrated system and components thereof that may be used for producing CAR T cells in accordance with a second embodiment of the present invention.

FIG. 7 is a block diagram showing an integrated system 300 and components thereof that may be used for producing CAR T cells. The integrated system 300, which has control electronics, user interface, hardware, software, and firmware (not shown), includes a first container or bag 102, a magnetic separator device 104, a cell incubation chamber 106, an acoustic separator device 302, a second container or bag 112 containing a buffer or solution for eluting target cells from the magnetic separator device 104, an incubation ingredient bank 114, a third container or bag 116 containing a buffer or solution for operating the acoustic separator device 302, a fourth container or bag 110 for the final cell product, and multiple fluidic lines 118-124 and 304-308 that provide fluidic interconnection between individual components in the integrated system 300. The integrated system 300 is analogous to the integrated system 100 shown in FIG. 1 except the second magnetic separator device 108 and the fluidic lines 126-130 connected thereto are replaced by the acoustic separator device 302 and the fluidic lines 304-308 connected thereto.

The first container or bag 102 holds a fluid sample that includes target cells 132 (e.g., T cells) with magnetic labels attached thereto. The fluid sample may contain whole blood, leukopak, PBMC, and/or other leukapheresis products containing the target cells 132 with magnetic labels attached thereto. The magnetic labels may be attached to the target cells 132 during an incubation process taking place in the same first container or bag 102.

The magnetic separator device 104, which is connected to the first container or bag 102 through the fluidic line 118, is used to extract the magnetically labeled target cells 132 from the fluid sample. The magnetic separator device 104 may have a structure that is identical or substantially similar to the magnetic separator device 188, the cross-sectional views of which are shown in FIGS. 3, 4 and described above.

The second container or bag 112, which is connected to an inlet of the magnetic separator device 104 through the fluidic line 120, contains the buffer or solution for eluting the magnetically labeled target cells 132 remained in the magnetic separator device 104 after the passage of the fluid sample. The buffer or solution in the second container or bag 112 may contain PBS based solution, culture media based solution, human serum, glucose, or any combination thereof.

The cell incubation chamber 106 may be used for cell genomic engineering, cell modification, cell transduction, or cell transfection. The cell incubation chamber 106 includes a cell container 134 therein that is connected to an outlet of the magnetic separator device 104 through the fluidic line 122. The cell container 134 contains the magnetically labeled target cells 132, the buffer or solution for eluting the cells from the magnetic separator device 104, and optionally one or more buffers or solutions from the incubation ingredient bank 114 connected to the cell container 134 through the fluidic line 124. The cell incubation chamber 106 may have one or more gas lines (e.g., $CO_2$) (not shown) connected thereto for providing an environment with desired gas composition (e.g., 5.0%±0.1% $CO_2$). The cell incubation chamber 106 may also have a heating and cooling mechanism (not shown) that can maintain the temperature constant (e.g., 37.0±0.1° C.) inside the chamber. Additionally, the cell incubation chamber 106 may also include an air circulation mechanism, such as a fan, to circulate air or other gas mixtures therein to make the temperature more uniform throughout the chamber 106. The cell container 134 and content therein may be heated or cooled by convection through the surrounding environment in the cell incubation chamber 106. The cell container 134 may also have a porous or permeable portion, such as membrane and air vent, that allows gas molecules in the surrounding environment to diffuse for flow through, thereby exposing the content of the cell container 134 to air or other gas mixtures inside the cell incubation chamber 106.

The incubation ingredient tank 114 may include one or more of the following items: culture media, vectors for cell transduction or transfection, lentivirus for transduction, buffers or solutions for non-viral transfection.

The cell incubation chamber 106 may further include means that can induce the target cell membrane to open, such as but not limited to cell electroporation, mechanical cell deformation, temperature, ultrasound, and optical, thereby allowing genetic materials to enter the target cells from the surrounding media in the cell container 134. Genetic materials can also be introduced into the target cells using droplet based genetic material injection or penetration through the target cell membrane.

The cell incubation chamber 106 may provide the environment for the transduction process. For example, lentivirus or other viruses may be used to transfer genomic materials into the target cells to induce chimeric antigen receptor (CAR) growth on the cell surface.

The acoustic separator device 302, which is connected to the cell container 134 inside the cell incubation chamber 106 through the fluidic line 304, is used to extract the target cells from the mixture of solutions and/or media used in the cell container 134 after genetic modification by transduction or transfection. The acoustic separator device 302 may have a structure that is identical or substantially similar to the acoustic separator device 428 shown in FIGS. 8A-8E.

FIG. 8A and FIGS. 8B-8D are a top view and corresponding cross-sectional views of an acoustic separator device 428 fabricated from a microfluidic chip 400, respectively. The microfluidic chip 400 includes a planar substrate 402, which has a first planar surface 404 and a second planar surface 406 opposite the first planar surface 404, and a lid 408 attached to the planar substrate 402 at the first planar surface 404. The planar substrate 402 includes a network of channels 411 recessed from the first planar surface 404 and substantially covered by the lid 408. The network of channels 411 includes a separation channel 410 having an upstream end and a downstream end, a side inlet port 412 for introducing a first fluid into the separation channel 410, a pair of side inlet channels 414 connecting the side inlet port 412 to the separation channel 410 at or near the upstream end thereof, a center inlet port 416 for introducing a second fluid into the separation channel 410, a center inlet channel 418 connecting the center inlet port 416 to the separation channel 410 at or near the upstream end thereof, a side outlet port 420 for extracting a third fluid from the separation channel 410, a pair of side outlet channels 422 connecting the side outlet port 420 to the separation channel 410 at or near the downstream end thereof, a center outlet port 424 for extracting a fourth fluid from the separation channel 410, a center outlet channel 426 connecting the center outlet port 424 to the separation channel 410 at or near the downstream end thereof.

Figure 8:
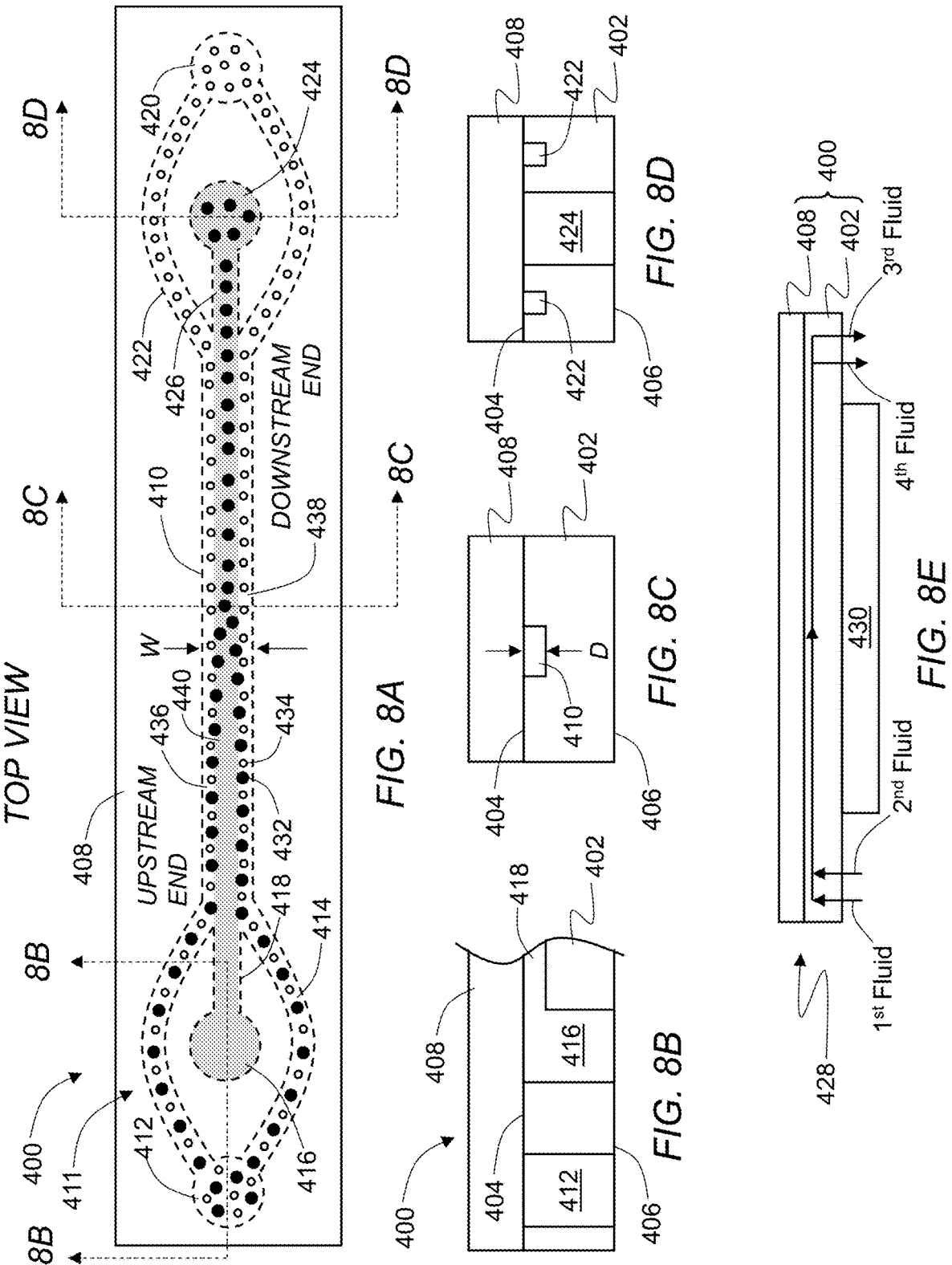
FIGS. 8A-8E are various views of an acoustic separator device that may be used to sort cells according to their physical properties.

The side and center inlet ports 412, 416 in FIG. 8B and the center outlet port 424 in FIG. 8D are opened to the exterior of the microfluidic chip 400 at the second planar surface 406 of the planar substrate 402. However, any of the ports 412, 416, 420, 424 may alternatively be opened to the exterior of the microfluidic chip 400 through the lid 408, which may include through-holes aligned with the respective port positions in the planar substrate 402.

Referring back to FIG. 8A, the separation channel 410 may have a linear shape with a nominal width, W, between two sidewalls thereof. W may be in the range of approximately 100 µm to 1 mm. One or more of the side inlet channels 414, the center inlet channel 418, the side outlet channels 422, and the center outlet channel 426 may be narrower than the nominal width of the separation channel 410. Referring to FIG. 8C, the separation channel 410 may have a nominal depth, D, as measured from the first planar surface 404. D may be in the range of approximately 50 µm to 500 µm. One or more of the side inlet channels 414, the center inlet channel 418, the side outlet channels 422, and the center outlet channel 426 may be shallower than the nominal depth of the separation channel 410.

The pair of side inlet channels 414 connect to the separation channel 410 at the two sidewalls thereof, near or at the upstream end. Therefore, the first fluid, which flows through the pair of side inlet channels 414, is introduced into the separation channel 410 as two streams flowing adjacent to the two sidewalls of the separation channel 410. The center inlet channel 418 connects to the separation channel 410 at or near the center thereof. The second fluid, which flows through the center inlet channels 418, is introduced into the center of the separation channel 410 and is interposed between the two streams of the first fluid at or near the upstream end of the separation channel 410.

The pair of side outlet channels 422 connect to the separation channel 410 at the two sidewalls thereof, at or near the downstream end. Therefore, the fluid flowing adjacent to the two sidewalls at or near the downstream end of the separation channel 410 is diverted by the pair of side outlet channels 422 to become the third fluid and exits the microfluidic chip 400 through the side outlet port 420. The remaining fluid at or near the center of the separation channel 410 not diverted by the pair of side outlet channels 422 becomes the fourth fluid and proceeds to flow through the center outlet channel 426 and exit the microfluidic chip 400 through the center outlet port 424.

FIG. 8E shows the fluidic paths through the microfluidic chip 400 in accordance with the port positions described above. The first and second fluids are introduced into the microfluidic chip 400 through the side and center inlet ports 412 and 416, respectively. The third and fourth fluids are extracted from the microfluidic chip 400 through the side and center outlet ports 420 and 424, respectively. The first fluid introduced through the side inlet port 412 may be a fluid sample that includes particles or biological objects with different sizes or acoustic contrasts for separation by acoustic radiation pressure, while the second fluid introduced through the center inlet port 416 may be a buffer fluid that does not contain any particles or biological objects. After passing through the separation channel 410, the third fluid extracted from the side outlet port 420 may include the particles or biological objects with relatively smaller sizes or smaller acoustic contrasts, while the fourth fluid extracted from the center outlet port 424 may include the particles or biological objects with relatively larger sizes or higher acoustic contrasts.

The microfluidic chip 400 is a part of the acoustic separator device 428, which further includes a piezoelectric transducer 430 attached to the microfluidic chip 400 as shown in FIG. 8E. The piezoelectric transducer 430 may be attached to the second planar surface 406 of the planar substrate 402, opposite the separation channel 410. The piezoelectric transducer 430 may alternatively be replaced by a cluster of two or more piezoelectric transducers disposed along the separation channel 410 and operating at the same frequency. The piezoelectric transducer 430 or the cluster of piezoelectric transducers may alternatively be attached to the microfluidic chip 400 at the exterior of the lid 408. Still alternatively, each of the second planar surface 406 of the planar substrate 402 and the exterior of the lid 408 independently has one or more piezoelectric transducers attached thereto.

The piezoelectric transducer 430 or cluster of piezoelectric transducers may receive power in the form of an oscillating voltage with a frequency in the range of 100 kHz to 100 MHz to generate acoustic pressure waves in the separation channel 410 between the two sidewalls thereof when a liquid is present. An acoustic standing wave may form in the separation channel 410 when the channel width, W, is an integer multiple of one-half wavelength of the acoustic pressure waves, which may depend on the excitation frequency of the power applied to the piezoelectric transducer 430 and the compressibility and density of the liquid in the separation channel 410. When W is equal to one-half wavelength of the acoustic waves generated by the piezoelectric transducer 430 or cluster of piezoelectric transducers, a standing wave is formed between the two sidewalls of the separation channel 410 with a single acoustic pressure node positioned along the center of the separation channel 410. Objects having relatively larger sizes and/or higher acoustic contrasts may move towards the pressure node at a faster rate, thereby allowing the separation of objects by size or acoustic contrast.

Operation of the acoustic separator device 428 under the condition of single pressure node will now be described with reference to FIGS. 8A-8E. After the completion of the transduction or transfection process, the fluid sample from the cell container 134, which contains the target cells 432 with modified genetic structure, small debris or undesirable biological objects 434 (i.e., non-target biological objects), if any, and the transduction or transfection media, is introduced into the side inlet port 412 via the fluidic line 304, while a buffer fluid is introduced into the center inlet port 416 from the third container or bag 116 via the fluidic line 306. The target cells and undesirable biological objects 432 and 434 may have sufficiently different physical sizes and/or acoustic contrasts, such as mass densities and compressibilities, to allow them to be separated by acoustic radiation pressure. For example, the target cells 432 may have a larger physical size and/or a higher acoustic contrast, such as a higher mass density and/or a lower compressibility, thereby allowing the acoustic radiation pressure to push the target cells 432 towards the pressure node located along the center of the separation channel 410 when operating under the single-node condition.

The fluid sample containing the target cells 432 and non-target biological objects 434 is introduced into the separation channel 410 at or near the upstream end thereof via the pair of side inlet channels 414 as two laminar streams 436 and 438 flowing adjacent to the sidewalls. The two laminar streams 436 and 438 of the fluid sample in the separation channel 410, which may behave like laminar flow, are interposed by the center stream 440 of buffer fluid from the center inlet port 416. The center stream 440 of buffer fluid may behave like laminar flow and act as a sheath fluid that retards or prevents the movement of the non-target biological objects 434 towards the pressure node positioned along the center of the separation channel 410. As the fluid sample progresses downstream in the separation channel 410, the acoustic radiation pressure pushes the target cells 432 into the center stream 440 and towards the pressure node positioned along the center of the separation channel 410, while the non-target biological objects 434 remain mostly in the two laminar streams 436 and 438 close to the sidewalls. At the downstream end of the separation channel 410, the target cells 432, which are carried by the buffer fluid, exit the acoustic separator device 428 through the center outlet port 424 to the fourth container or bag 110. The depleted fluid sample, which may include the non-target biological objects 434 and flows near the sidewalls as the laminar streams 436 and 438, is diverted to the side outlet port 420 through the pair of side outlet channels 422.

Referring back to FIG. 7, the third container or bag 116, which is connected to an inlet of the acoustic separator device 302 through the fluidic line 306, contains a buffer or solution that may act as a sheath fluid during the acoustic separation of the genetically modified target cells in the acoustic separator device 302. The buffer or solution may also be used as a storage fluid to preserve the genetically modified target cells in the fourth container for bag 110. The buffer or solution in the third container or bag 116 may contain PBS based solution, saline based solution, human serum, glucose, or any combination thereof.

The fourth container or bag 110, which is connected to an outlet of the acoustic separator device 302 through the fluidic line 308, contains the genetically modified target cells in a buffer or solution that may be intravenously administered to patients.

The network of the fluidic lines 118-124, 304-308, the containers or bags 102, 110, 112, 116, the cell container 134, and the fluidic line passing through the magnetic separator device 104, and the acoustic separator device 302 may be constructed, interconnected, and supplied as an integrated disposable tubing set, which may be sterile and sealed from the surrounding environment.

With continued reference to FIG. 7, the process begins by providing the first container or bag 102 that includes therein a first fluid sample containing the magnetically labeled target cells 132. For previously frozen samples, the first fluid sample may be prepared by first thawing the frozen samples and then extract the target cells and other biological objects, if any, from the thawed sample fluid by centrifugation. The resultant target cells and other biological objects, if any, are resuspended in a buffer fluid and filtered using a mesh size of between 15 and 100 μm. A reagent containing the magnetic labels is added to the filtered buffer fluid containing the target cells, thereby forming the first fluid sample. Alternatively, the target cells may be magnetically labeled through an indirect process by first adding a reagent containing intermediate links that attach to the target cells prior to adding the reagent containing the magnetic labels that attach to intermediate links.

The first fluid sample is flowed into the inlet of the magnetic separator device 104 through the fluidic line 118 for the magnetic sorting process. As the first fluid sample flows through the magnetic separator device 104, the magnetically labeled target cells 132 are retained in the magnetic separator device 104 by a magnetic field, while the depleted first fluid sample exit the magnetic separator device 104 to a waste container or bag (not shown). After the first fluid sample completely passes through the magnetic separator device 104, the magnetic field acting on the magnetically labeled target cells 132 is reduced or removed, and a first eluant, such as a buffer fluid, in the second container or bag 112 flows through the fluidic line 120 and into the magnetic separator device 104 to elute the magnetically labeled target cells 132 into the cell container 134 via the fluidic line 122.

Additionally, one or more solutions from the incubation ingredient tank 114, such as but not limited to culture media, vectors for cell transduction or transfection, lentivirus for transduction, buffers or solutions for non-viral transfection, are injected into the cell container 134 through the fluidic line 124 for modifying the genetic structure of the magnetically labeled target cells 132. The magnetically labeled target cells 132 (e.g., T cells) can be transduced to express a CAR by contacting the target cells with vectors that carry CAR constructs, including viral vectors, such as lentivirus and retrovirus, and non-viral vectors, such as plasmid, lipid nanoparticles, and mRNA.

The transduction or transfection process is carried out in the cell incubation chamber 106 while the magnetically labeled target cells 132 are immersed in a transduction or transfection media, which comprises the first eluant and the one or more solutions from the incubation ingredient tank 114. The temperature and gas composition inside the cell incubation chamber 106 can be controlled during the transduction or transfection process. For example, the temperature and gas composition inside the cell incubation chamber 106 may be maintained at 37.0±0.1° C. and 5.0%±0.1% $CO_2$, respectively, for a period of time ranging from 10 min to 72 hrs while the genetic structure of the magnetically labeled target cells 132 is being modified in the cell container 134.

After the transduction or transfection process is completed, a buffer fluid for facilitating the subsequent acoustic sorting process may be added to the transduction or transfection media in the cell container 134 from the incubation ingredient tank 114. The mixture of the transduction or transfection media and the buffer fluid for facilitating the acoustic sorting process, if any, forms the second fluid sample containing the genetically modified target cells.

The second fluid sample is then flowed into the inlet of the acoustic separator device 302 through the fluidic line 304 to extract the genetically modified target cells by the acoustic sorting process. Using the acoustic separator device 428 shown in FIGS. 8A-8E as an example, the second fluid sample containing the genetically modified target cells is introduced into the side inlet port 412 via the fluidic line 304, while a buffer fluid is introduced into the center inlet port 416 from the third container or bag 116 via the fluidic line 306. The second fluid sample containing the genetically modified target cells 432 and non-target biological objects 434, if any, is introduced into the separation channel 410 at or near the upstream end thereof via the pair of side inlet channels 414 as two laminar streams 436 and 438 flowing adjacent to the sidewalls. The two laminar streams 436 and 438 of the second fluid sample in the separation channel 410 are interposed by the center stream 440 of buffer fluid from the center inlet port 416. The center stream 440 of buffer fluid may behave like laminar flow and act as a sheath fluid that retards or prevents the movement of the non-target biological objects 434 towards the pressure node positioned along the center of the separation channel 410. As the second fluid sample progresses downstream in the separation channel 410, the acoustic radiation pressure pushes the genetically modified target cells 432 into the center stream 440 and towards the pressure node positioned along the center of the separation channel 410, while the non-target biological objects 434 remain mostly in the two laminar streams 436 and 438 close to the sidewalls. At the downstream end of the separation channel 410, the genetically modified target cells 432, which are carried by the buffer fluid, exit the acoustic separator device 428 through the center outlet port 424 and to the fourth container or bag 110 via the fluidic line 308.

The depleted second fluid sample, which may include the non-target biological objects 434 and flows near the sidewalls as the laminar streams 436 and 438, is diverted to the side outlet port 420 through the pair of side outlet channels 422.

After the acoustic sorting process is completed, the fourth container or bag 110 containing the genetically modified target cells may be severed from the rest of the integrated system 300 without exposing its content to atmosphere. The content in the third container or bag 300 may be intravenously administered to patients.

Figure 9:
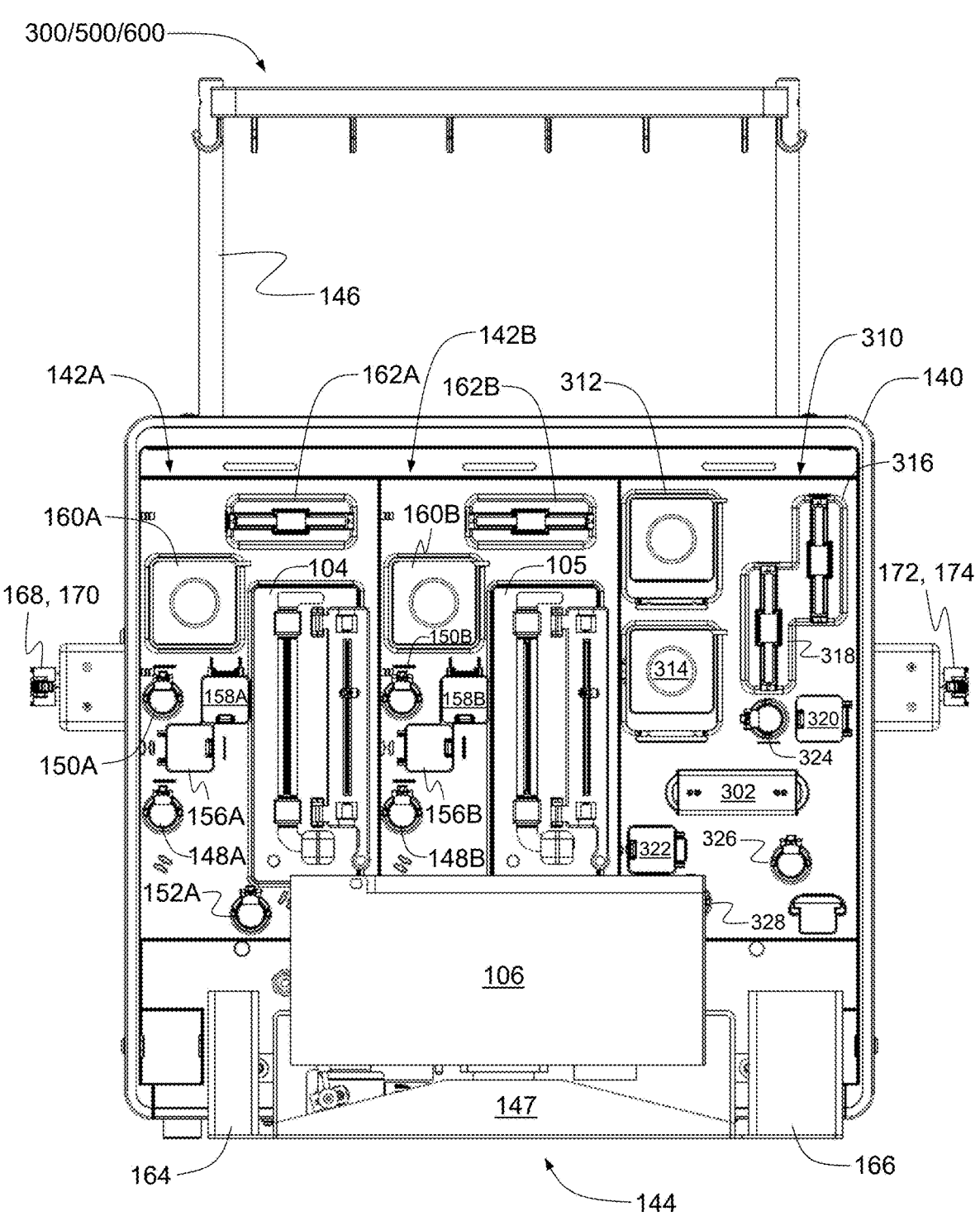
FIG. 9 is a frontal view of an integrated system that may be used to produce CAR T cells from whole blood or leukapheresis products in accordance with the first, second, and third embodiments of the present invention.

FIG. 9 is a frontal view of the integrated system 300 that may be used to produce CAR T cells from whole blood or samples containing T cells in accordance with the process described above. The system 300 may utilize a closed fluidic assembly to become a closed processing system that can be deployed in a facility that lacks a stringent sterile or clean environment, such as the treatment facility, thereby alleviating much of the common logistic issues encountered in the autologous treatment.

FIG. 9 shows the automated production system 300 including a shell or housing structure 140, first and second magnetic separator modules 142A, 142B and an acoustic separator module 310 residing in the housing structure 140, an incubation module 144, a sample rack 146 mounted on top of the housing structure 140, and first and second sample bag holders 164, 166. The fluidic lines and sample bags connected thereto, which may be supplied as an integrated disposable tubing set, and the computer used for controlling the system 300 are omitted in the drawing in order to present an unobstructive view of the magnetic separator modules 142A, 142B and the acoustic separator module 310. The production system 300 is analogous to the system 100 shown in FIG. 2 except for the replacement of the magnetic separator module 142C by the acoustic separator module 310.

The incubation module 144 includes an incubation chamber 106 sitting on top of a rocker base 147. Each of the magnetic separator modules 142A, 142B includes a first pinch valve 148A, 148B, a second pinch valve 150A, 150B, a third pinch valve 152A, 152B, a fourth pinch valve 154A, 154B, a first air detector 156A, 156B, a second air detector 158A, 158B, a peristaltic pump 160A, 160B, a blockage sensor 162A, 162B, and a magnetic separator device 104, 105. The acoustic separator module 310 includes first and second peristaltic pumps 312, 314, first and second blockage sensors 316, 318, first and second air detectors 320, 322, an acoustic separator device 302, first, second, and third pinch valves 324-328.

The system 300 may also include additional pinch valves 168, 170 disposed on one side of the housing structure 140 and additional pinch valves 172, 174 disposed on the other side of the housing structure 140. The electromechanical components 104-106, 147, 148A/B-162A/B, 168-174, 312-328 may be controlled or automated by a computer or microprocessor (not shown).

Each of the magnetic separator devices 104, 105 may have a structure that is identical or substantially similar to the magnetic separator device 188 shown in FIGS. 3 and 4 and described above. Other magnetic flux sources and column-free magnetic separator devices, such as those disclosed in U.S. application Ser. No. 18/072,362, which is incorporated herein by reference, may also be used to separate the magnetically labeled target cells from the fluid sample.

The acoustic separator device 302 may have a structure that is identical or substantially similar to the acoustic separator device 428 shown in FIGS. 8A-8E and described above.

The incubation module 144 includes the cell incubation chamber 106 sitting atop of the rocker base 147. The incubation chamber 106 has a heater that can uniformly maintain the temperature inside the chamber 106 between room temperature and 50° C. The $CO_2$ concentration inside the chamber 106 can be varied between 0 and 10% to provide an optimal environment for cells. The rocker base 147 may move the chamber 106 at a speed between 2 rpm and 4 rpm. The swaying motion of the chamber 106 caused by the rocker base 147 may facilitate uniform mixing of the fluid content inside the cell container 134. The rocker base 147 may remain stationary during cell activation, transduction, or expansion process. After the incubation process, the rocker base 147 may effectuate the cell container 134 inside the chamber 106 to sway, causing the fluid in the cell container 134 to rinse cells off the surface of the cell container 134. The rocker base 147 may also be used to facilitate draining of the cell container 134 by tilting the incubation chamber 106 to a fixed position to allow the end of the outlet tube to reach the bottom of the fluid inside the cell container 134.

The system 300 has a modular design comprising two magnetic separator modules 142A, 142B, one acoustic separator module 310, and one incubation module 144. The modules 142A, 142B, 144, and 310 may be fluidically connected in series, parallel, or a combination thereof by a closed fluidic assembly that includes sample bags, cell containers, acoustic separator device, and all fluidic lines including conduits passing through the magnetic separator devices.

Figure 10:
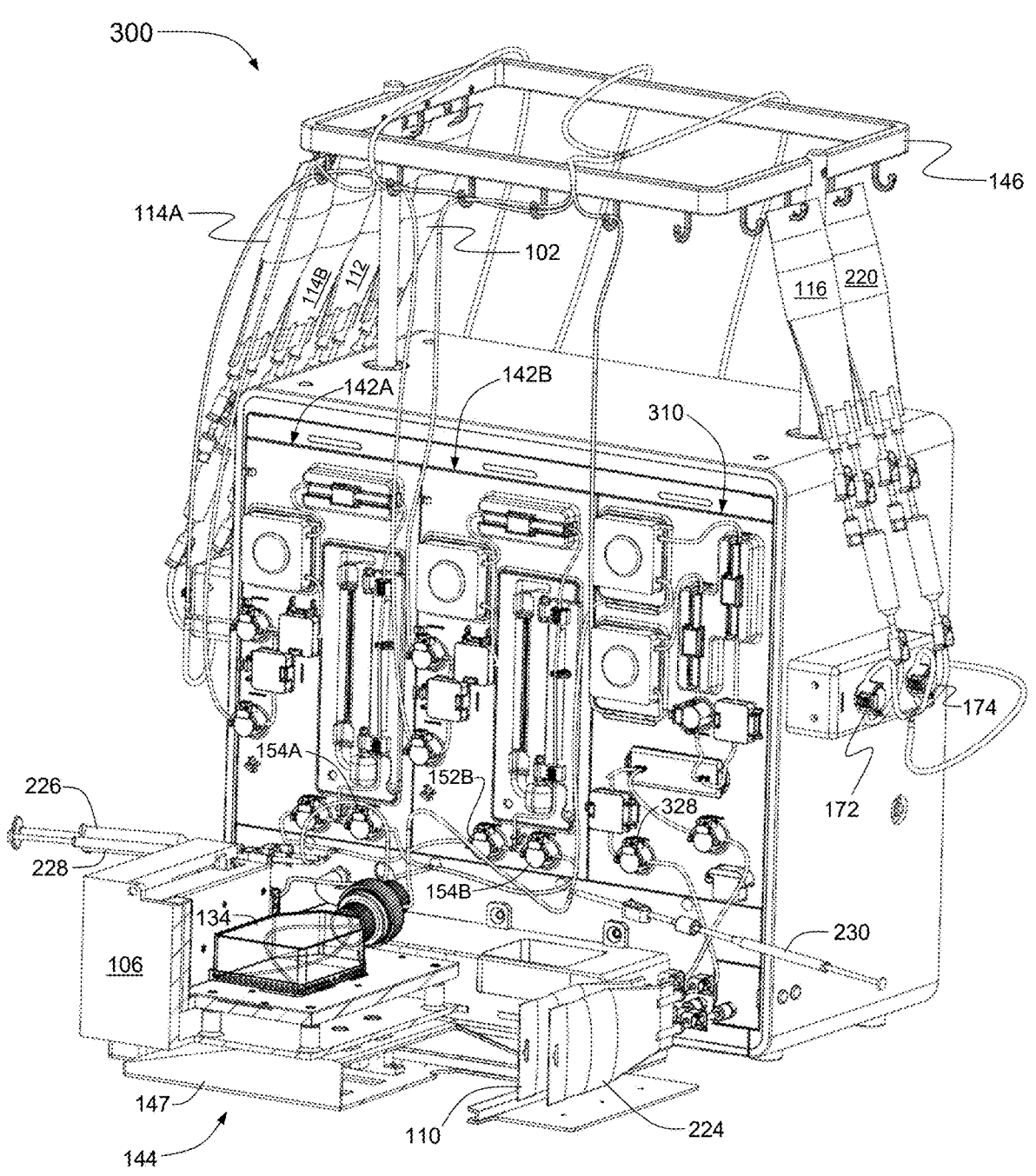
FIG. 10 is a perspective view of the integrated system of FIG. 9 using a closed fluidic assembly in the form of an integrated tubing set for manufacturing CAR T cells in accordance with the second embodiment of the present invention.
Figure 11:
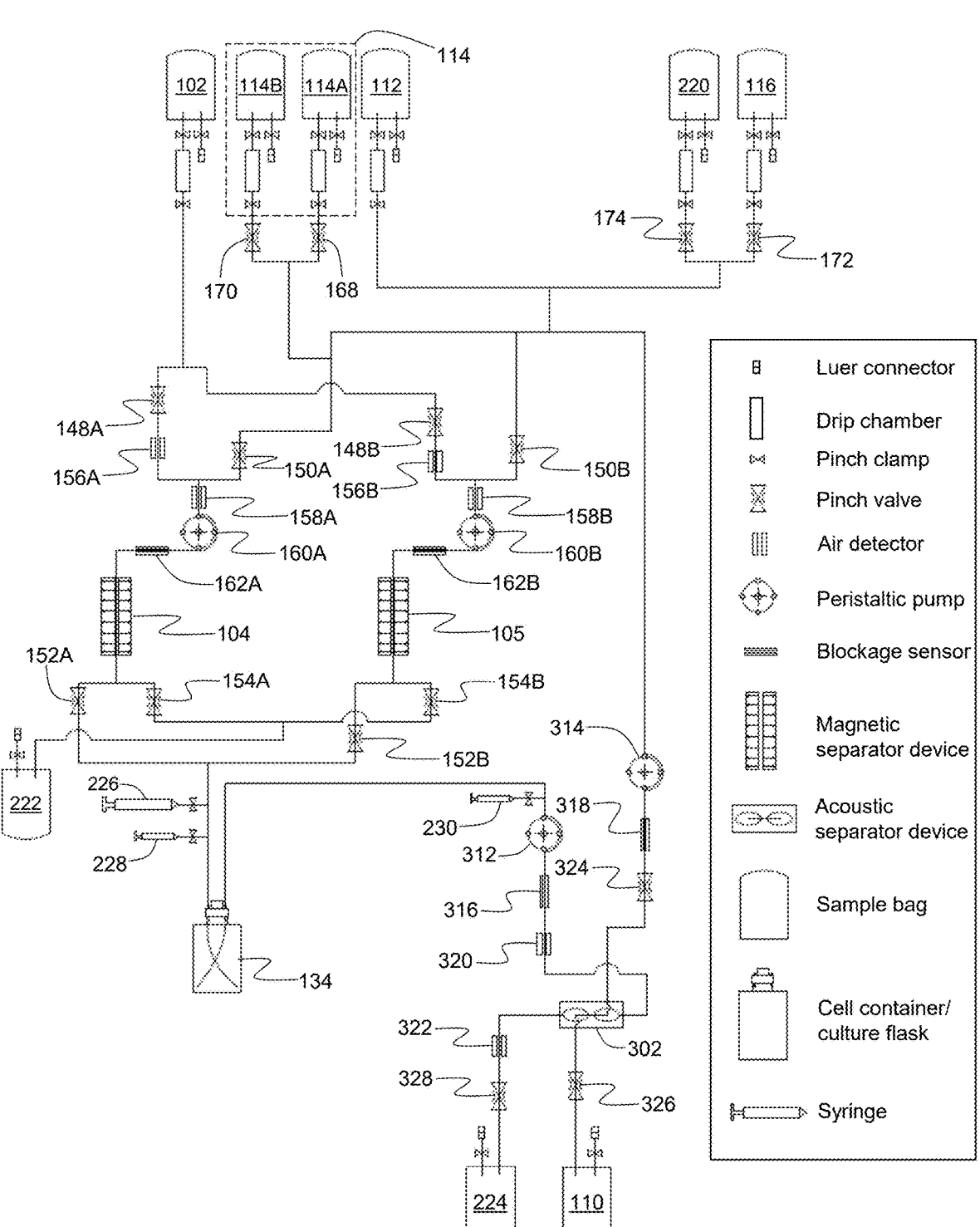
FIG. 11 is fluidic circuit diagram corresponding to the integrated system of FIG. 10.

FIG. 10 is a perspective view of the system 300 using a closed fluidic assembly in the form of an integrated tubing set for manufacturing CAR T cells. For reasons of legibility, electromechanical components labeled in FIG. 9 are not relabeled in the drawing to clearly show the routing of fluidic lines. The perspective view also shows the pinch valves 152B, 154A, 154B, 328 that are previously blocked by the cell incubation chamber 106 and the pinch valves 172, 174 disposed on the side of the housing structure 140 in the frontal view of FIG. 9. The lid and a section of one side wall of the incubation chamber 106 are further removed to expose the cell container 134 in the form of a common cell culture flask inside the chamber 106. The cap of the cell culture flask 134 contains an air filter that is vented to the environment inside the incubation chamber 106 while preserving sterility inside the flask 134. The second bag holder 166 is also omitted from the drawing to show the sample bags 110, 224 inside the holder 166. FIG. 11 is a fluidic circuit diagram corresponding to the system 300 shown in FIG. 10.

Referring to FIGS. 9-11, the fluidic assembly of the system 300 is arranged to use the first and second magnetic separator devices 104, 105 that are fluidically coupled in parallel to extract the magnetically labeled target cells (e.g., T cells) from the first fluid sample in the magnetic sorting process and the acoustic separator device 302 for the subsequent acoustic sorting process. The use of two magnetic separator devices 104, 105 for the magnetic sorting process enables the system 300 to increase the sorting throughput and accommodate a larger volume of the first fluid sample, such as whole blood.

The first, second, third, and fourth containers or bags 102, 112, 116, 110 are in the form of sample bags. The sample bags 102 and 112 are both fluidically connected to the inlets of the first and second magnetic separator devices 104, 105. In addition to the sample bag 116, another sample bag 220, which may also contain cryopreservation solution, storage media, PBS based solution, saline based solution, human serum, glucose, or any combination thereof, is also fluidically connected to the inlet of the acoustic separator device 302. The incubation ingredient bank 114 includes at least two sample bags 114A, 114B fluidically connected to the cell container 134 through the magnetic separator devices 104, 105. Each of the sample bags 114A, 114B may include culture media, vectors for cell transduction or transfection, lentivirus for transduction, buffers or solutions for non-viral transfection, or cell activation reagent. Prior to the transduction or transfection process, the target T cells in the cell container 134 may be activated by flowing a cell activation reagent (e.g., solution containing CD3/CD28 magnetic beads) from one of the sample bags 114A, 114B into the cell container 134.

The fluidic assembly of the system 300 further includes a sample bag 222 fluidically connected to the outlets of the first and second magnetic separator devices 104, 105 for collecting waste from the devices 104, 105, and another sample bag 224 fluidically connected to the outlet of the acoustic separator device 302 for collecting waste from the device 302. The sample bag 222 for collecting waste from the first and second magnetic separator devices 104, 105 may be placed in the first bag holder 164. The sample bags 110, 224 for respectively collecting the final cell product and waste from the acoustic separator device 302 may be placed in the second bag holder 166. All other sample bags 102, 112, 114A, 114B, 116, 220, which provide materials for the manufacturing process, may be hung on the sample rack 146. The fluidic assembly of the system 300 may include additional sample bags for various purposes. Each of the sample bags 102, 110, 112, 114A, 114B, 116, 220-224 may have an inlet port with a Luer connector connected thereto and an outlet port with a drip chamber connected thereto. Additionally, the fluid flowing through the inlet and outlet ports of each sample bag may be controlled or regulated by one or more manual pinch clamps attached thereto.

The fluidic assembly of the system 300 may also include syringes 226, 228, 230. The syringes 226, 228, which may be fluidically connected to the inlet of the cell container 134, may be used to extract a sample of the magnetically separated target cells after the magnetic sorting process or may inject culture media, vectors for cell transduction or transfection, lentivirus for transduction, buffers or solutions for non-viral transfection, or cell activation reagent into the cell container 134. The syringe 230, which may be fluidically connected to the outlet of the cell container 134, may be used to extract a sample of the genetically modified target cells after the transduction or transfection process is completed.

With continued reference to FIG. 11, the fluidic circuit corresponding to the system 300 includes the sample bags 102, 110, 112, 114A, 114B, 116, 220-224, the syringes 226-230, the cell container 134, and the acoustic separator device 302, all interconnected by a network of fluidic lines that pass through the electromechanical components, such as the pinch valves 148A/B-154A/B, 168-172, 324-328, the air detectors 156A/B, 158A/B, 320, 322, the blockage sensors 162A, 162B, 316, 318, the peristaltic pumps 160A, 160B, 312, 314, and the magnetic separator devices 104, 105. The sample bags 102, 110, 112, 114A, 114B, 116, 220-224, the syringes 226-230, the cell container 134, the acoustic separator device 302, and the network of fluidic lines including the conduits passing through the magnetic separator devices

104, 105 may be constructed, interconnected, sterilized, and supplied as an integrated disposable set. The electromechanical components of the system 300 are external to the tubing set and therefore do not come into contact the fluid in the tubing set.

The first container or sample bag 102, which may contain target cells for processing, is fluidically connected to the inlet of the conduit passing through the first magnetic separator device 104 by one or more fluidic lines that pass through the first pinch valve 148A, the first air detector 156A, the second air detector 158A, the peristaltic pump 160A, and the blockage sensor 162A, and is also fluidically connected to the inlet of the conduit passing through the second magnetic separator device 105 by one or more fluidic lines that pass through the first pinch valve 148B, the first air detector 156B, the second air detector 158B, the peristaltic pump 160B, and the blockage sensor 162B. The second container or sample bag 112, which may contain a buffer solution or culture media, is fluidically connected to the inlet of the conduit passing through the first magnetic separator device 104 by one or more fluidic lines that pass through the second pinch valve 150A, the second air detector 158A, the peristaltic pump 160A, and the blockage sensor 162A, and is also fluidically connected to the inlet of the conduit passing through the second magnetic separator device 105 through one or more fluidic lines that pass through the second pinch valve 150B, the second air detector 158B, the peristaltic pump 160B, and the blockage sensor 162B.

The inlet of the cell container 134 is fluidically connected to the outlet of the conduit passing through the first magnetic separator device 104 by one or more fluidic lines that pass through the third pinch valve 152A, and is also fluidically connected to the outlet of the conduit passing through the second magnetic separator device 105 by one or more fluidic lines that pass through the third pinch valve 152B. The syringes 226, 228 may be fluidically connected to a fluidic line between the inlet of the cell container 134 and the third pinch valves 152A, 152B. The sample bag 222, which may store waste fluid such as sample fluid after target cell extraction, is fluidically connected to the outlet of the conduit passing through the first magnetic separator device 104 by one or more fluidic lines that pass through the fourth pinch valve 154A, and is also fluidically connected to the outlet of the conduit passing through the second magnetic separator device 105 by one or more fluidic lines that pass through the fourth pinch valve 154B.

The outlet of the cell container 134 is fluidically connected to the inlet of the acoustic separator device 302 (e.g., side inlet port 412 of FIG. 8A) by one or more fluidic lines that pass through the first peristaltic pump 312, the first blockage sensor 316, and the first air detector 320. The syringe 230 may be fluidically connected to a fluidic line connected to the outlet of the cell container 134. The third container or sample bag 116 is fluidically connected to the inlet of the acoustic separator device 302 (e.g., center inlet port 416 of FIG. 8A) by one or more fluidic lines that pass through the pinch valve 172, the second peristaltic pump 314, the second blockage sensor 318, and the first pinch valve 324. The sample bag 220 is fluidically connected to the inlet of the acoustic separator device 302 (e.g., center inlet port 416 of FIG. 8A) by one or more fluidic lines that pass through the pinch valve 174, the second peristaltic pump 314, the second blockage sensor 318, and the first pinch valve 324.

The fourth container or sample bag 110 is fluidically connected to the outlet of the acoustic separator device 302 (e.g., center outlet port 424 of FIG. 8A) by one or more fluidic lines that pass through the second pinch valve 326. The sample bag 224, which may be used to receive waste fluid, is fluidically connected to the outlet of the acoustic separator device 302 (e.g., side outlet port 420 of FIG. 8A) by one or more fluidic lines that pass through the second air detector 322 and the third pinch valve 328.

The sample bag 114A of the incubation ingredient bank 114 is fluidically connected to the inlet of the cell container 134 by one or more fluidic lines that pass through the pinch valve 168, the second pinch valve 150A, the second air detector 158A, the peristaltic pump 160A, the blockage sensor 162A, the first magnetic separator device 104, and the third pinch valve 152A, and by one or more fluidic lines that pass through the pinch valve 168, the second pinch valve 150B, the second air detector 158B, the peristaltic pump 160B, the blockage sensor 162B, the second magnetic separator device 105, and the third pinch valve 152B. Similarly, the sample bag 114B of the incubation ingredient bank 114 is fluidically connected to the inlet of the cell container 134 by one or more fluidic lines that pass through the pinch valve 170, the second pinch valve 150A, the second air detector 158A, the peristaltic pump 160A, the blockage sensor 162A, the first magnetic separator device 104, and the third pinch valve 152A, and by one or more fluidic lines that pass through the pinch valve 170, the second pinch valve 150B, the second air detector 158B, the peristaltic pump 160B, the blockage sensor 162B, the second magnetic separator device 105, and the third pinch valve 152B.

Embodiment 3: Negative Magnetic Selection and Acoustic Purification

This embodiment uses a magnetic separator device to isolate or extract nonmagnetic target cells from magnetically labeled non-target cells for genetic modification, which may take place in a cell incubator, and then uses an acoustic separator device to purify the genetically modified target cells.

Figure 12:
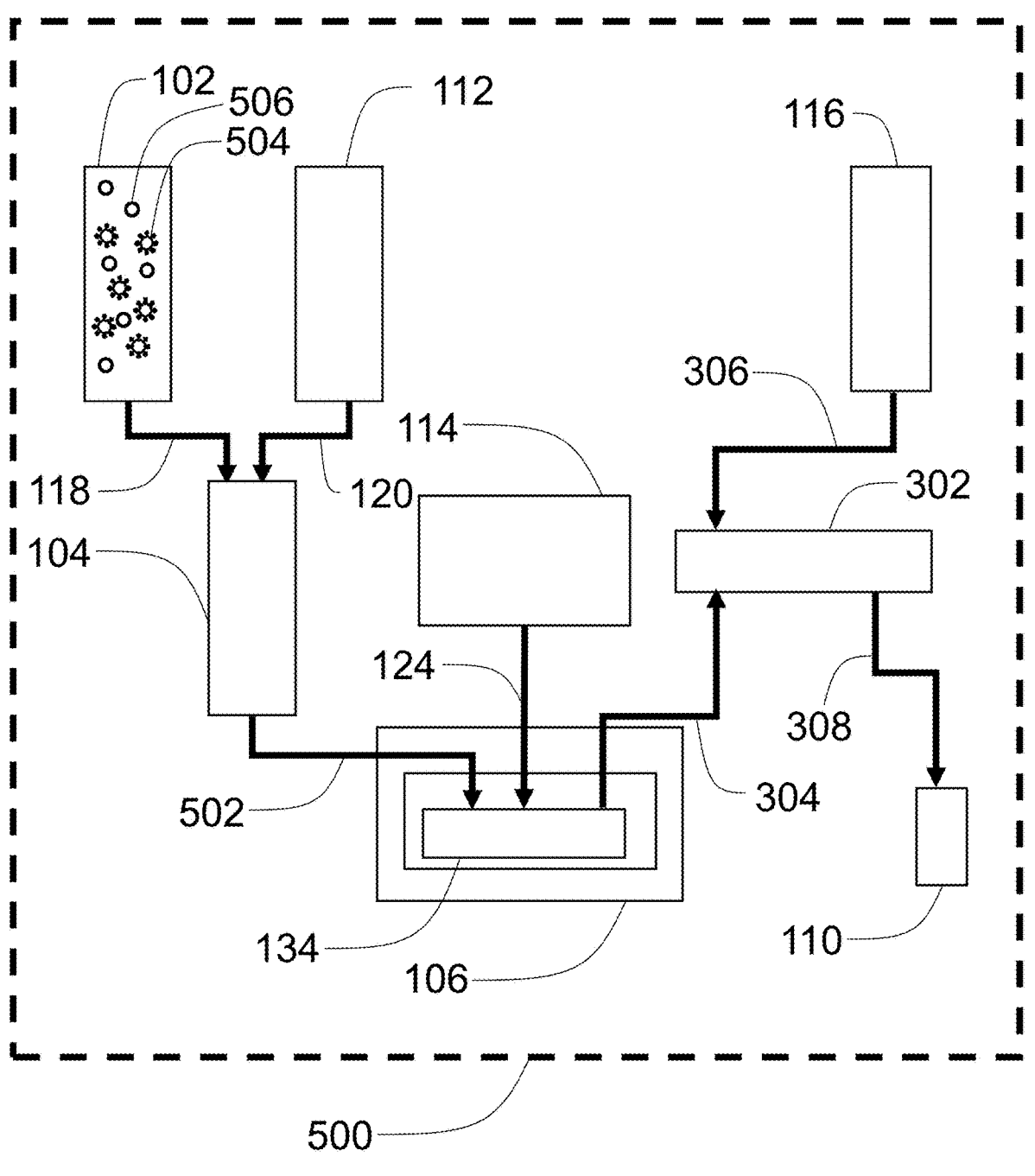
FIG. 12 is a block diagram showing an integrated system and components thereof that may be used for producing CAR T cells in accordance with the third embodiment of the present invention.

FIG. 12 is a block diagram showing an integrated system 500 and components thereof that may be used for producing CAR T cells. The integrated system 500, which has control electronics, user interface, hardware, software, and firmware (not shown), includes a first container or bag 102, a magnetic separator device 104, a cell incubation chamber 106, an acoustic separator device 302, a second container or bag 112 containing a buffer or solution for eluting magnetically labeled non-target cells from the magnetic separator device 104, an incubation ingredient bank 114, a third container or bag 116 containing a buffer or solution for operating the acoustic separator device 302, a fourth container or bag 110 for the final cell product, and multiple fluidic lines 118, 120, 124, 304-308, 502 that provide fluidic interconnection between individual components in the integrated system 500. The components 102-106, 110-120, 124, 134, 302-308 of the integrated system 500 are analogous to the components 110-120, 124, 134, 302-308 of the integrated system 300, respectively, as shown in FIG. 4 and described above, except for the replacement of the fluidic line 122 by the fluidic line 502 to accommodate the negative selection process (i.e., non-target cells being magnetically labeled).

The first container or bag 102 holds a fluid sample that includes non-target cells 504 with magnetic labels attached thereto and target cells 506 without magnetic labels. The fluid sample may contain whole blood, leukopak, PBMC, and/or other cell suspension that has non-target cells 504 with magnetic labels attached thereto. Magnetic labels may be attached to the non-target cells 504 during an incubation process taking place in the same sample container or bag 102.

The magnetic separator device 104, which is connected to the first container or bag 102 through the fluidic line 118, is used to extract the magnetically labeled non-target cells 504 from the fluid sample. The magnetic separator device 104 may have a structure that is identical or substantially similar to the magnetic separator device 188, the cross-sectional views of which are shown in FIGS. 3 and 4 and described above.

The second container or bag 112, which is connected to an inlet of the magnetic separator device 104 through the fluidic line 120, contains the buffer or solution for eluting the magnetically labeled non-target cells 504 remained in the magnetic separator device 104 after the passage of the fluid sample. The buffer or solution in the second container or bag 112 may contain PBS based solution, culture media based solution, human serum, glucose, or any combination thereof.

The cell incubation chamber 106 may be used for cell genomic engineering, cell modification, cell transduction, or cell transfection. The cell incubation chamber 106 includes a cell container 134 therein that is connected to an outlet of the magnetic separator device 104 through the fluidic line 502. The cell container 134 contains the non-magnetic target cells 506, and one or more buffers or solutions from the incubation ingredient bank 114 connected to the cell container 134 through the fluidic line 124. The cell incubation chamber 106 may have one or more gas lines (e.g., $CO_2$) (not shown) connected thereto for providing an environment with desired gas composition (e.g., $5.0\% \pm 0.1\%$ $CO_2$). The cell incubation chamber 106 may also have a heating and cooling mechanism (not shown) that can maintain the temperature constant (e.g., $37.0 \pm 0.1°$ C.) inside the chamber. Additionally, the cell incubation chamber 106 may also include an air circulation mechanism, such as a fan, to circulate air or other gas mixtures therein to make the temperature more uniform throughout the chamber 106. The cell container 134 and content therein may be heated or cooled by convection through the surrounding environment in the cell incubation chamber 106. The cell container 134 may also have a porous or permeable portion, such as membrane and air vent, that allows gas molecules in the surrounding environment to diffuse for flow through, thereby exposing the content of the cell container 134 to air or other gas mixtures inside the cell incubation chamber 106.

The incubation ingredient tank 114 may include one or more of the following items: culture media, vectors for cell transduction or transfection, lentivirus for transduction, buffers or solutions for non-viral transfection.

The cell incubation chamber 106 may further include means that can induce the target cell membrane to open, such as but not limited to cell electroporation, mechanical cell deformation, temperature, ultrasound, and optical, thereby allowing genetic materials to enter the target cells from the surrounding media in the cell container 134. Genetic materials can also be introduced into the target cells using droplet based genetic material injection or penetration through the target cell membrane.

The cell incubation chamber 106 may provide the environment for the transduction process. For example, lentivirus or other viruses may be used to transfer genomic materials into the target cells to induce chimeric antigen receptor (CAR) growth on the cell surface.

The acoustic separator device 302, which is connected to the cell container 134 inside the cell incubation chamber 106 through the fluidic line 304, is used to extract the target cells from the mixture of solutions and/or media used in the cell container 134 after genetic modification by transduction or transfection. The acoustic separator device 302 may have a structure that is identical or substantially similar to the acoustic separator device 428 shown in FIGS. 8A-8E and described above.

The third container or bag 116, which is connected to an inlet of the acoustic separator device 302 through the fluidic line 306, contains a buffer or solution that may act as a sheath fluid during the acoustic separation of the genetically modified target cells in the acoustic separator device 302. The buffer or solution may also be used as a storage fluid to preserve the genetically modified target cells in the fourth container for bag 110. The buffer or solution in the third container or bag 116 may contain PBS based solution, saline based solution, human serum, glucose, or any combination thereof.

The fourth container or bag 110, which is connected to an outlet of the acoustic separator device 302 through the fluidic line 308, contains the genetically modified target cells in a buffer or solution that may be intravenously administered to patients.

The network of the fluidic lines 118, 120, 124, 304-308, 502, the containers or bags 102, 110, 112, 116, the cell container 134, and the fluidic line passing through the magnetic separator device 104, and the acoustic separator device 302 may be constructed, interconnected, and supplied as an integrated disposable tubing set, which may be sterile and sealed from the surrounding environment.

With continued reference to FIG. 12, the process begins by providing the first container or bag 102 that includes therein a first fluid sample containing the magnetically labeled non-target cells 504 and the non-magnetic target cells 506. The first fluid sample is flowed into the inlet of the magnetic separator device 104 through the fluidic line 118 for the magnetic sorting process.

As the first fluid sample flows through the magnetic separator device 104, the magnetically labeled non-target cells 504 are retained in the magnetic separator device 104 by a magnetic field, while the non-magnetic target cells 506, which is carried by the depleted fluid sample (i.e., without the magnetically labeled non-target cells 504), exit the magnetic separator device 104 to the cell container 134 via the fluidic line 502. One or more solutions from the incubation ingredient tank 114, such as but not limited to culture media, vectors for cell transduction or transfection, lentivirus for transduction, buffers or solutions for non-viral transfection, are injected into the cell container 134 through the fluidic line 124 for modifying the genetic structure of the non-magnetic target cells 506. The non-magnetic target cells 506 (e.g., T cells) can be transduced to express a CAR by contacting the target cells with vectors that carry CAR constructs, including viral vectors, such as lentivirus and retrovirus, and non-viral vectors, such as plasmid, lipid nanoparticles, and mRNA.

The transduction or transfection process is carried out in the cell incubation chamber 106 while the target cells 506 is immersed in a transduction or transfection media, which comprises the first eluant and the one or more solutions from the incubation ingredient tank 114. The temperature and gas composition inside the cell incubation chamber 106 can be controlled during the transduction or transfection process. For example, the temperature and gas composition inside the cell incubation chamber 3c may be maintained at 37.0±0.1° C. and 5.0%±0.1% $CO_2$, respectively, for a period of time ranging from 10 min to 72 hrs while the genetic structure of the target cells 506 is being modified in the cell container 134.

After the transduction or transfection process is completed, a buffer fluid for facilitating the subsequent acoustic sorting process may be added to the transduction or transfection media in the cell container 134 from the incubation ingredient tank 114. The mixture of the transduction or transfection media and the buffer fluid for facilitating the acoustic sorting process, if any, forms the second fluid sample containing the genetically modified target cells.

The second fluid sample is then flowed into the inlet of the acoustic separator device 302 through the fluidic line 304 to extract the genetically modified target cells by the acoustic sorting process. Using the acoustic separator device 428 shown in FIGS. 8A-85E as an example, the second fluid sample containing the genetically modified target cells is introduced into the side inlet port 412 via the fluidic line 304, while a buffer fluid is introduced into the center inlet port 416 from the third container or bag 116 via the fluidic line 306. The second fluid sample containing the genetically modified target cells 432 and non-target biological objects 434, if any, is introduced into the separation channel 410 at or near the upstream end thereof via the pair of side inlet channels 414 as two laminar streams 436 and 438 flowing adjacent to the sidewalls. The two laminar streams 436 and 438 of the second fluid sample in the separation channel 410 are interposed by the center stream 440 of buffer fluid from the center inlet port 416. The center stream 440 of buffer fluid may behave like laminar flow and act as a sheath fluid that retards or prevents the movement of the non-target biological objects 434 towards the pressure node positioned along the center of the separation channel 410. As the second fluid sample progresses downstream in the separation channel 410, the acoustic radiation pressure pushes the genetically modified target cells 432 into the center stream 440 and towards the pressure node positioned along the center of the separation channel 410, while the non-target biological objects 434 remain mostly in the two laminar streams 436 and 438 close to the sidewalls. At the downstream end of the separation channel 410, the genetically modified target cells 432, which are carried by the buffer fluid, exit the acoustic separator device 428 through the center outlet port 424 and to the fourth container or bag 110 via the fluidic line 308. The depleted second fluid sample, which may include the non-target biological objects 434 and flows near the sidewalls as the laminar streams 436 and 438, is diverted to the side outlet port 420 through the pair of side outlet channels 422.

After the acoustic sorting process is completed, the fourth container or bag 110 containing the genetically modified target cells may be severed from the rest of the integrated system 500 without exposing its content to atmosphere. The content in the fourth container or bag 110 may be intravenously administered to patients.

FIG. 9 is a frontal view of the integrated system 500 that may be used to produce CAR T cells from whole blood or samples containing T cells in accordance with the process described above. The system 500 may utilize a closed fluidic assembly to become a closed processing system that can be deployed in a facility that lacks a stringent sterile or clean environment, such as the treatment facility, thereby alleviating much of the common logistic issues encountered in the autologous treatment.

FIG. 9 shows the automated production system 500 including a shell or housing structure 140, first and second magnetic separator modules 142A, 142B and an acoustic separator module 310 residing in the housing structure 140, an incubation module 144, a sample rack 146 mounted on top of the housing structure 140, and first and second sample bag holders 164, 166. The fluidic lines and sample bags connected thereto, which may be supplied as an integrated disposable tubing set, and the computer used for controlling the system 500 are omitted in the drawing in order to present an unobstructive view of the magnetic separator modules 142A, 142B and the acoustic separator module 310. The production system 500 is analogous to the system 300 except for the routing of the fluidic lines to accommodate the negative selection of magnetic sorting process as will be shown below.

The incubation module 144 includes an incubation chamber 106 sitting on top of a rocker base 147. Each of the magnetic separator modules 142A, 142B includes a first pinch valve 148A, 148B, a second pinch valve 150A, 150B, a third pinch valve 152A, 152B, a fourth pinch valve 154A, 154B, a first air detector 156A, 156B, a second air detector 158A, 158B, a peristaltic pump 160A, 160B, a blockage sensor 162A, 162B, and a magnetic separator device 104, 105. The acoustic separator module 310 includes first and second peristaltic pumps 312, 314, first and second blockage sensors 316, 318, first and second air detectors 320, 322, an acoustic separator device 302, first, second, and third pinch valves 324-328.

The system 500 may also include additional pinch valves 168, 170 disposed on one side of the housing structure 140 and additional pinch valves 172, 174 disposed on the other side of the housing structure 140. The electromechanical components 104-106, 147, 148A/B-162A/B, 168-174, 312-328 may be controlled or automated by a computer or microprocessor (not shown).

Each of the magnetic separator devices 104, 105 may have a structure that is identical or substantially similar to the magnetic separator device 188 shown in FIGS. 3 and 4 and described above. Other magnetic flux sources and column-free magnetic separator devices, such as those disclosed in U.S. application Ser. No. 18/072,362, which is incorporated herein by reference, may also be used to separate the magnetically labeled target cells from the fluid sample.

The acoustic separator device 302 may have a structure that is identical or substantially similar to the acoustic separator device 428 shown in FIGS. 8A-8E and described above.

The incubation module 144 includes the cell incubation chamber 106 sitting atop of the rocker base 147. The incubation chamber 106 has a heater that can uniformly maintain the temperature inside the chamber 106 between room temperature and 50° C. The $CO_2$ concentration inside the chamber 106 can be varied between 0 and 10% to provide an optimal environment for cells. The rocker base 147 may move the chamber 106 at a speed between 2 rpm and 4 rpm. The swaying motion of the chamber 106 caused by the rocker base 147 may facilitate uniform mixing of the fluid content inside the cell container 134. The rocker base 147 may remain stationary during cell activation, transduction, or expansion process. After the incubation process, the rocker base 147 may effectuate the cell container 134 inside the chamber 106 to sway, causing the fluid in the cell container 134 to rinse cells off the surface of the cell container 134. The rocker base 147 may also be used to facilitate draining of the cell container 134 by tilting the incubation chamber 106 to a fixed position to allow the end of the outlet tube to reach the bottom of the fluid inside the cell container 134.

The system 500 has a modular design comprising two magnetic separator modules 142A, 142B, one acoustic separator module 310, and one incubation module 144. The modules 142A, 142B, 144, and 310 may be fluidically connected in series, parallel, or a combination thereof by a closed fluidic assembly that includes sample bags, cell containers, acoustic separator device, and all fluidic lines including conduits passing through the magnetic separator devices.

Figure 13:
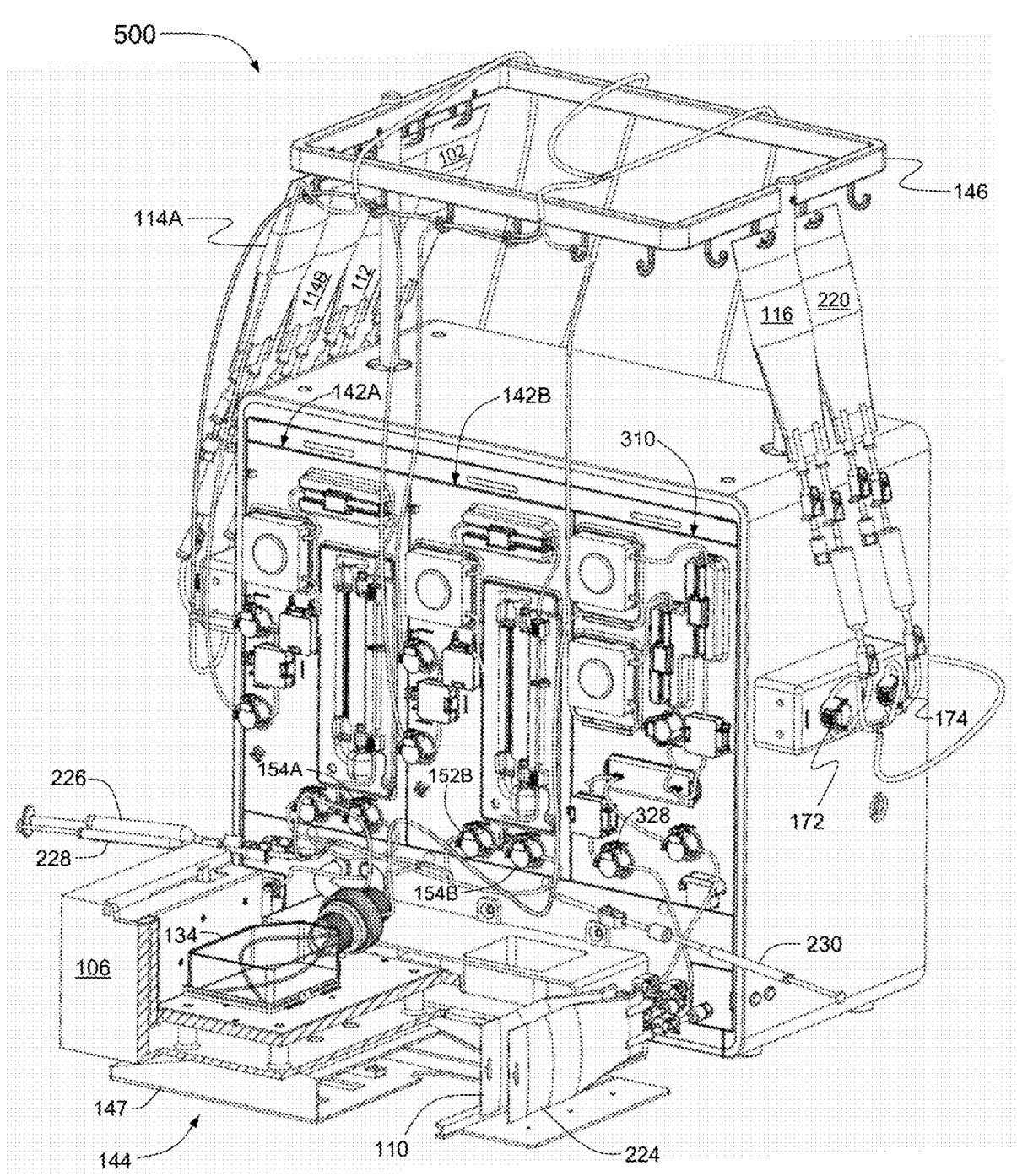
FIG. 13 is a perspective view of the integrated system of FIG. 9 using a closed fluidic assembly in the form of an integrated tubing set for manufacturing CAR T cells in accordance with the third embodiment of the present invention.
Figure 14:
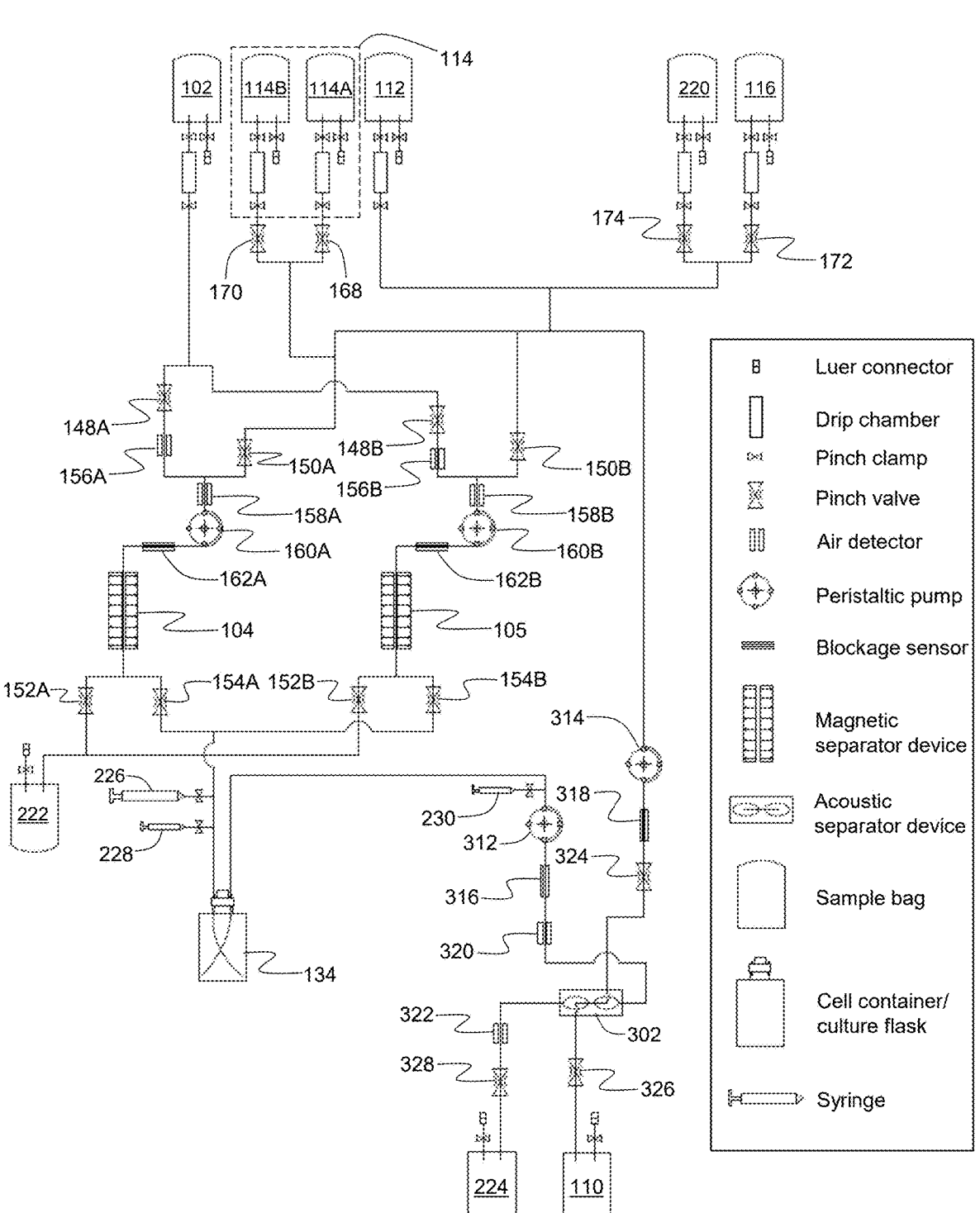
FIG. 14 is fluidic circuit diagram corresponding to the integrated system of FIG. 13.

FIG. 13 is a perspective view of the system 500 using a closed fluidic assembly in the form of an integrated tubing set for manufacturing CAR T cells. For reasons of legibility, electromechanical components labeled in FIG. 9 are not relabeled in the drawing to clearly show the routing of fluidic lines. The perspective view also shows the pinch valves 152B, 154A, 154B, 328 that are previously blocked by the cell incubation chamber 106 and the pinch valves 172, 174 disposed on one side of the housing structure 140 in the frontal view of FIG. 9. The lid and a section of the side wall of the incubation chamber 106 are further removed to expose the cell container 134 in the form of a common cell culture flask inside the chamber 106. The cap of the cell culture flask 134 contains an air filter that is vented to the environment inside the incubation chamber 106 while preserving sterility inside the flask 134. The second bag holder 166 is also omitted from the drawing to show the sample bags 110, 224 inside the holder 166. FIG. 14 is a fluidic circuit diagram corresponding to the system 500 shown in FIG. 13.

Referring to FIGS. 9, 13, 14, the fluidic assembly of the system 500 is arranged to use the first and second magnetic separator devices 104, 105 that are fluidically coupled in parallel to extract the magnetically labeled non-target cells from the first fluid sample in the magnetic sorting process and the acoustic separator device 302 for purifying the nonmagnetic target cells. The use of two magnetic separator devices 104, 105 for the magnetic sorting process enables the system 500 to increase the sorting throughput and accommodate a larger volume of the first fluid sample.

The first, second, third, and fourth containers or bags 102, 112, 116, 110 are in the form of sample bags. The sample bags 102 and 112 are both fluidically connected to the inlets of the first and second magnetic separator devices 104, 105. In addition to the sample bag 116, another sample bag 220, which may also contain cryopreservation solution, storage media, PBS based solution, saline based solution, human serum, glucose, or any combination thereof, is also fluidically connected to the inlet of the acoustic separator device 302. The incubation ingredient bank 114 includes at least two sample bags 114A, 114B fluidically connected to the cell container 134 through the magnetic separator devices 104, 105. Each of the sample bags 114A, 114B may include culture media, vectors for cell transduction or transfection, lentivirus for transduction, buffers or solutions for non-viral transfection, or cell activation reagent. Prior to the transduction or transfection process, the target T cells in the cell container 134 may be activated by flowing a cell activation reagent (e.g., solution containing CD3/CD28 magnetic beads) from one of the sample bags 114A, 114B into the cell container 134.

The fluidic assembly of the system 500 further includes a sample bag 222 fluidically connected to the outlets of the first and second magnetic separator devices 104, 105 for collecting waste from the devices 104, 105, and another sample bag 224 fluidically connected to the outlet of the acoustic separator device 302 for collecting waste from the device 302. The sample bag 222 for collecting waste from the first and second magnetic separator devices 104, 105 may be placed in the first bag holder 164. The sample bags 110, 224 for respectively collecting the final cell product and waste from the acoustic separator device 302 may be placed in the second bag holder 166. All other sample bags 102, 112, 114A, 114B, 116, 220, which provide materials for the manufacturing process, may be hung on the sample rack 146. The fluidic assembly of the system 500 may include additional sample bags for various purposes. Each of the sample bags 102, 110, 112, 114A, 114B, 116, 220-224 may have an inlet port with a Luer connector connected thereto and an outlet port with a drip chamber connected thereto. Additionally, the fluid flowing through the inlet and outlet ports of each sample bag may be controlled or regulated by one or more manual pinch clamps attached thereto.

The fluidic assembly of the system 500 may also include syringes 226, 228, 230. The syringes 226, 228, which may be fluidically connected to the inlet of the cell container 134, may be used to extract a sample of the magnetically separated target cells after the magnetic sorting process or may inject culture media, vectors for cell transduction or transfection, lentivirus for transduction, buffers or solutions for non-viral transfection, or cell activation reagent into the cell container 134. The syringe 230, which may be fluidically connected to the outlet of the cell container 134, may be used to extract a sample of the genetically modified target cells after the transduction or transfection process is completed.

With continued reference to FIG. 14, the fluidic circuit corresponding to the system 500 includes the sample bags 102, 110, 112, 114A, 114B, 116, 220-224, the syringes 226-230, the cell container 134, and the acoustic separator device 302, all interconnected by a network of fluidic lines that pass through the electromechanical components, such as the pinch valves 148A/B-154A/B, 168-172, 324-328, the air detectors 156A/B, 158A/B, 320, 322, the blockage sensors 162A, 162B, 316, 318, the peristaltic pumps 160A, 160B, 312, 314, and the magnetic separator devices 104, 105. The sample bags 102, 110, 112, 114A, 114B, 116, 220-224, the syringes 226-230, the cell container 134, the acoustic separator device 302, and the network of fluidic lines including the conduits passing through the magnetic separator devices 104, 105 may be constructed, interconnected, sterilized, and supplied as an integrated disposable set. The electromechanical components of the system 500 are external to the tubing set and therefore do not come into contact the fluid in the tubing set.

The first container or sample bag 102, which may contain target cells for processing, is fluidically connected to the inlet of the conduit passing through the first magnetic separator device 104 by one or more fluidic lines that pass through the first pinch valve 148A, the first air detector 156A, the second air detector 158A, the peristaltic pump 160A, and the blockage sensor 162A, and is also fluidically connected to the inlet of the conduit passing through the second magnetic separator device 105 by one or more fluidic lines that pass through the first pinch valve 148B, the first air detector 156B, the second air detector 158B, the peristaltic pump 160B, and the blockage sensor 162B. The second container or sample bag 112, which may contain a buffer solution or culture media, is fluidically connected to the inlet of the conduit passing through the first magnetic separator device 104 by one or more fluidic lines that pass through the second pinch valve 150A, the second air detector 158A, the peristaltic pump 160A, and the blockage sensor 162A, and is also fluidically connected to the inlet of the conduit passing through the second magnetic separator device 105 through one or more fluidic lines that pass through the second pinch valve 150B, the second air detector 158B, the peristaltic pump 160B, and the blockage sensor 162B.

The inlet of the cell container 134 is fluidically connected to the outlet of the conduit passing through the first magnetic separator device 104 by one or more fluidic lines that pass through the fourth pinch valve 154A, and is also fluidically connected to the outlet of the conduit passing through the second magnetic separator device 105 by one or more fluidic lines that pass through the fourth pinch valve 154B. The syringes 226, 228 may be fluidically connected to a fluidic line between the inlet of the cell container 134 and the fourth pinch valves 154A, 154B. The sample bag 222, which may store waste fluid containing magnetically labeled non-target cells, is fluidically connected to the outlet of the conduit passing through the first magnetic separator device 104 by one or more fluidic lines that pass through the third pinch valve 152A, and is also fluidically connected to the outlet of the conduit passing through the second magnetic separator device 105 by one or more fluidic lines that pass through the third pinch valve 152B.

The outlet of the cell container 134 is fluidically connected to the inlet of the acoustic separator device 302 (e.g., side inlet port 412 of FIG. 8A) by one or more fluidic lines that pass through the first peristaltic pump 312, the first blockage sensor 316, and the first air detector 320. The syringe 230 may be fluidically connected to a fluidic line connected to the outlet of the cell container 134. The third container or sample bag 116 is fluidically connected to the inlet of the acoustic separator device 302 (e.g., center inlet port 416 of FIG. 8A) by one or more fluidic lines that pass through the pinch valve 172, the second peristaltic pump 314, the second blockage sensor 318, and the first pinch valve 324. The sample bag 220 is fluidically connected to the inlet of the acoustic separator device 302 (e.g., center inlet port 416 of FIG. 8A) by one or more fluidic lines that pass through the pinch valve 174, the second peristaltic pump 314, the second blockage sensor 318, and the first pinch valve 324.

The fourth container or sample bag 110 is fluidically connected to the outlet of the acoustic separator device 302 (e.g., center outlet port 424 of FIG. 8A) by one or more fluidic lines that pass through the second pinch valve 326. The sample bag 224, which may be used to receive waste fluid, is fluidically connected to the outlet of the acoustic separator device 302 (e.g., side outlet port 420 of FIG. 8A) by one or more fluidic lines that pass through the second air detector 322 and the third pinch valve 328.

The sample bag 114A of the incubation ingredient bank 114 is fluidically connected to the inlet of the cell container 134 by one or more fluidic lines that pass through the pinch valve 168, the second pinch valve 150A, the second air detector 158A, the peristaltic pump 160A, the blockage sensor 162A, the first magnetic separator device 104, and the fourth pinch valve 154A, and by one or more fluidic lines that pass through the pinch valve 168, the second pinch valve 150B, the second air detector 158B, the peristaltic pump 160B, the blockage sensor 162B, the second magnetic separator device 105, and the fourth pinch valve 154B. Similarly, the sample bag 114B of the incubation ingredient bank 114 is fluidically connected to the inlet of the cell container 134 by one or more fluidic lines that pass through the pinch valve 170, the second pinch valve 150A, the second air detector 158A, the peristaltic pump 160A, the first magnetic separator device 104, and the fourth pinch valve 154A, and by one or more fluidic lines that pass through the pinch valve 170, the second pinch valve 150B, the second air detector 158B, the peristaltic pump 160B, the blockage sensor 162B, the second magnetic separator device 105, and the fourth pinch valve 154B.

Embodiment 4: Positive Magnetic Selection, Delabeling, Acoustic Purification

This embodiment uses a first magnetic separator device to isolate or extract magnetically labeled target cells, a cell incubator to genetically modify the magnetically labeled target cells and remove the magnetic labels from the target cells, especially when using larger magnetic labels, and an acoustic separator device to purify the genetically modified target cells.

Figure 15:
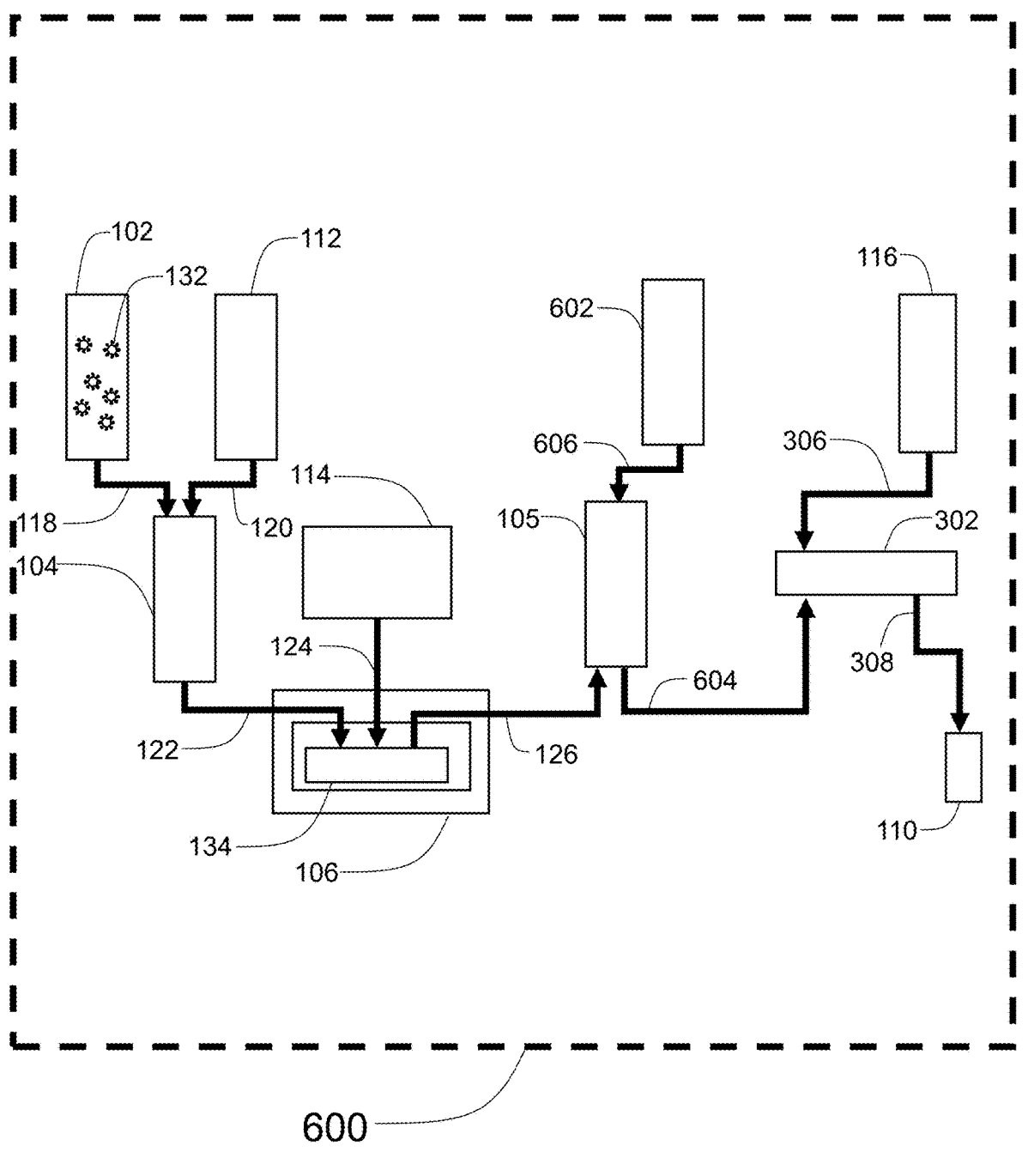
FIG. 15 is a block diagram showing an integrated system and components thereof that may be used for producing CAR T cells in accordance with the fourth embodiment of the present invention.

FIG. 15 is a block diagram showing an integrated system 600 and components thereof that may be used for producing CAR T cells. The integrated system 600, which has control electronics, user interface, hardware, software, and firmware (not shown), includes a first container or bag 102, a first magnetic separator device 104, a cell incubation chamber 106, a second magnetic separator device 105, an acoustic separator device 302, a second container or bag 112 containing a buffer or solution for eluting target cells from the first magnetic separator device 104, an incubation ingredient bank 114, a third container or bag 116 containing a buffer or solution for operating the acoustic separator device 302, a fourth container or bag 110 for final cell product, a fifth container or bag 602 containing a buffer or solution for eluting magnetic labels from the second magnetic separator device 105 and/or for priming the second magnetic separator device 105, and multiple fluidic lines 118-126, 306, 308, 604, 606 that provide fluidic interconnection between individual components in the integrated system 600.

The first container or bag 102 holds a fluid sample that includes target cells 132 (e.g., T cells) with magnetic labels attached thereto. The fluid sample may contain whole blood, leukopak, PBMC, and/or other leukapheresis products that contain the target cells 132 with magnetic labels attached thereto. The magnetic labels may be attached to the target cells 132 during an incubation process taking place in the same first container or bag 102.

The first magnetic separator device 104, which is connected to the first container or bag 102 through the fluidic line 118, is used to extract the magnetically labeled target cells 132 from the fluid sample. The first magnetic separator device 104 may have a structure that is identical or substantially similar to the magnetic separator device 188, the cross-sectional views of which are shown in FIGS. 3, 4 and described above.

The second container or bag 112, which is connected to an inlet of the first magnetic separator device 104 through the fluidic line 120, contains the buffer or solution for eluting the magnetically labeled target cells 132 remained in the first magnetic separator device 104 after the passage of the fluid sample. The buffer or solution in the second container or bag 112 may contain PBS based solution, culture media based solution, human serum, glucose, or any combination thereof.

The cell incubation chamber 106 may be used for cell genomic engineering, cell modification, cell transduction, or cell transfection. The cell incubation chamber 106 includes a cell container 134 therein that is connected to an outlet of the first magnetic separator device 104 through the fluidic line 122. The cell container 134 contains the magnetically labeled target cells 132, the buffer or solution for eluting the cells from the first magnetic separator device 104, and optionally one or more buffers or solutions from the incubation ingredient bank 114 connected to the cell container 134 through the fluidic line 124. The cell incubation chamber 106 may have one or more gas lines (e.g., $CO_2$) (not shown) connected thereto for providing an environment with desired gas composition (e.g., 5.0%±0.1% $CO_2$). The cell incubation chamber 106 may also have a heating and cooling mechanism (not shown) that can maintain the temperature constant (e.g., 37.0±0.1° C.) inside the chamber. Additionally, the cell incubation chamber 106 may also include an air circulation mechanism, such as a fan, to circulate air or other gas mixtures therein to make the temperature more uniform throughout the chamber 106. The cell container 134 and content therein may be heated or cooled by convection through the surrounding environment in the cell incubation chamber 106. The cell container 134 may also have a porous or permeable portion, such as membrane and air vent, that allows gas molecules in the surrounding environment to diffuse for flow through, thereby exposing the content of the cell container 134 to air or other gas mixtures inside the cell incubation chamber 106.

The incubation ingredient tank 114 may include one or more of the following items: culture media, vectors for cell transduction or transfection, lentivirus for transduction, buffers or solutions for non-viral transfection, reagent for removing magnetic labels from the target cells in a delabeling process.

The cell incubation chamber 106 may further include means that can induce the target cell membrane to open, such as but not limited to cell electroporation, mechanical cell deformation, temperature, ultrasound, and optical, thereby allowing genetic materials to enter the target cells from the surrounding media in the cell container 134. Genetic materials can also be introduced into the target cells using droplet based genetic material injection or penetration through the target cell membrane.

The cell incubation chamber 106 may provide the environment for the transduction process. For example, lentivirus or other viruses may be used to transfer genomic materials into the target cells to induce chimeric antigen receptor (CAR) growth on the cell surface. The magnetic labels attached to the target cells 132 may also be removed from the target cells in the cell container 134 before, during, or after the genetic modification process (e.g., transduction or transfection) by adding the delabeling reagent to the cell container 134 from the incubation ingredient tank 114.

The second magnetic separator device 105, which is connected to the cell container 134 inside the cell incubation chamber 106 through the fluidic line 126, is used to remove the free magnetic labels that have been stripped from the genetically modified target cells in the mixture of solutions and/or media in the cell container 134, which may include the buffer for eluting the genetically modified target cells from the first magnetic separator device 104, one or more reagents for transduction or transfection, and a reagent for delabeling the target cells 132. The second magnetic separator device 105 retains the free magnetic labels as the mixture of solutions and/or media, which contains genetically modified target cells that have been delabeled, flows through the second magnetic separator device 105 and into an inlet of the acoustic separator device 302 through the fluidic line 604. The second magnetic separator device 105 may have a structure that is identical or substantially similar to a magnetic separator device 188, the cross-sectional views of which are shown in FIGS. 3, 4 and described above.

In an alternative scheme, the delabeled target cells may flow from the second magnetic separator device 105 to a container or bag before further flowing to the inlet of the acoustic separator device 302. The container or bag may serve as a reservoir to temporarily store the fluid therein to allow the second magnetic separator device 105 at its downstream and the acoustic separator device 302 at its upstream to operate at different flow rates if needed.

The fifth container or bag 602, which is connected to an inlet of the second magnetic separator device 105 through the fluidic line 606, contains the buffer or solution for eluting the free magnetic labels remained in the second magnetic separator device 105 after the passage of the fluid sample. The buffer or solution in the fifth container or bag 602 may contain PBS based solution, culture media based solution, human serum, glucose, or any combination thereof.

The acoustic separator device 302, which is connected to an outlet of the second magnetic separator device 105 through the fluidic line 604, is used to extract the genetically modified target cells from the mixture of solutions and/or media outputted from the second magnetic separator device 105. The acoustic separator device 302 may have a structure that is identical or substantially similar to the acoustic separator device 428 shown in FIGS. 8A-8E.

The third container or bag 116, which is connected to an inlet of the acoustic separator device 302 through the fluidic line 306, contains a buffer or solution that may act as a sheath fluid during the acoustic separation of the genetically modified target cells in the acoustic separator device 302. The buffer or solution may also be used as a storage fluid to preserve the genetically modified target cells in the fourth container for bag 110. The buffer or solution in the third container or bag 116 may contain PBS based solution, saline based solution, human serum, glucose, or any combination thereof.

The fourth container or bag 110, which is connected to an outlet of the acoustic separator device 302 through the fluidic line 308, contains the genetically modified target cells in a buffer or solution that may be intravenously administered to patients.

The network of the fluidic lines 118-126, 306, 308, 604, 606, the containers or bags 102, 110, 112, 116, 602 the cell container 134, and the fluidic lines passing through the first and second magnetic separator devices 104, 105, and the acoustic separator device 302 may be constructed, interconnected, and supplied as an integrated disposable tubing set, which may be sterile and sealed from the surrounding environment.

With continued reference to FIG. 15, the process begins by providing the first container or bag 102 that includes therein a first fluid sample containing the magnetically labeled target cells 132. For previously frozen samples, the first fluid sample may be prepared by first thawing the frozen samples and then extract the target cells and other biological objects, if any, from the thawed sample fluid by centrifugation. The resultant target cells and other biological objects, if any, are resuspended in a buffer fluid and filtered using a mesh size of between 15 and 100 μm. A reagent containing the magnetic labels is added to the filtered buffer fluid containing the target cells, thereby forming the first fluid sample. Alternatively, the target cells may be magnetically labeled through an indirect process by first adding a reagent containing intermediate links that attach to the target cells prior to adding the reagent containing the magnetic labels that attach to intermediate links.

The first fluid sample is flowed into the inlet of the magnetic separator device 104 through the fluidic line 118 for the magnetic sorting process. As the first fluid sample flows through the magnetic separator device 104, the magnetically labeled target cells 132 are retained in the magnetic separator device 104 by a magnetic field, while the depleted first fluid sample exit the magnetic separator device 104 to a waste container or bag (not shown). After the first fluid sample completely passes through the magnetic separator device 104, the magnetic field acting on the magnetically labeled target cells 132 is reduced or removed, and a first eluant, such as a buffer fluid, in the second container or bag 112 flows through the fluidic line 120 and into the magnetic separator device 104 to elute the magnetically labeled target cells 132 into the cell container 134 via the fluidic line 122. Additionally, one or more solutions from the incubation ingredient tank 114, such as but not limited to culture media, vectors for cell transduction or transfection, lentivirus for transduction, buffers or solutions for non-viral transfection, are injected into the cell container 134 through the fluidic line 124 for modifying the genetic structure of the magnetically labeled target cells 132. The magnetically labeled target cells 132 (e.g., T cells) can be transduced to express a CAR by contacting the target cells with vectors that carry CAR constructs, including viral vectors, such as lentivirus and retrovirus, and non-viral vectors, such as plasmid, lipid nanoparticles, and mRNA.

The transduction or transfection process is carried out in the cell incubation chamber 106 while the magnetically labeled target cells 132 is immersed in a transduction or transfection media, which comprises the first eluant and the one or more solutions from the incubation ingredient tank 114. The temperature and gas composition inside the cell incubation chamber 106 can be controlled during the transduction or transfection process. For example, the temperature and gas composition inside the cell incubation chamber 106 may be maintained at 37.0±0.1° C. and 5.0%±0.1% $CO_2$, respectively, for a period of time ranging from 10 min to 72 hrs while the genetic structure of the magnetically labeled target cells 132 is being modified in the cell container 134. A reagent may be injected into the cell container 134 from the incubation ingredient tank 114 for removing magnetic labels from the target cells after completion of the transduction or transfection process. Alternatively, this delabeling process may be carried out before or during the transduction or transfection process.

After the genetic modification and delabeling processes of the target cells are completed, a buffer fluid for facilitating the subsequent acoustic sorting process may be added to the transduction or transfection media and the delabeling reagent in the cell container 134 from the incubation ingredient tank 114. The mixture of the transduction or transfection media, the delabeling reagent, and the buffer fluid for facilitating the acoustic sorting process, if any, forms the second fluid sample containing the genetically modified target cells without magnetic labels.

The second fluid sample is then flowed into the inlet of the second magnetic separator device 105 through the fluidic line 126 to extract the free magnetic labels by the second magnetic sorting process. As the second fluid sample flows through the second magnetic separator device 105, the free magnetic labels, including those that are removed from the genetically modified target cells, are retained in the second magnetic separator device 105 by a magnetic field, while the genetically modified target cells, which is carried by the depleted second fluid sample (i.e., without the free magnetic labels), exit the second magnetic separator device 105 to the acoustic separator device 302 through the fluidic line 604.

Using the acoustic separator device 428 shown in FIGS. 8A-8E as an example, the depleted second fluid sample containing the genetically modified target cells 432 is introduced into the side inlet port 412 via the fluidic line 604, while a buffer fluid is introduced into the center inlet port 416 from the third container or bag 116 via the fluidic line 306. The depleted second fluid sample containing the genetically modified target cells 432 and non-target biological objects/debris 434, if any, is introduced into the separation channel 410 at or near the upstream end thereof via the pair of side inlet channels 414 as two laminar streams 436 and 438 flowing adjacent to the sidewalls. The two laminar streams 436 and 438 of the depleted second fluid sample in the separation channel 410 are interposed by the center stream 440 of buffer fluid from the center inlet port 416. The center stream 440 of buffer fluid may behave like laminar flow and act as a sheath fluid that retards or prevents the movement of the non-target biological objects/debris 434 towards the pressure node positioned along the center of the separation channel 410. As the depleted second fluid sample progresses downstream in the separation channel 410, the acoustic radiation pressure pushes the genetically modified target cells 432 into the center stream 440 and towards the pressure node positioned along the center of the separation channel 410, while the non-target biological objects/debris 434 remain mostly in the two laminar streams 436 and 438 close to the sidewalls. At the downstream end of the separation channel 410, the genetically modified target cells 432, which are carried by the buffer fluid, exit the acoustic separator device 428 through the center outlet port 424 and to the fourth container or bag 110 via the fluidic line 308. The further depleted second fluid sample, which may include the non-target biological objects/debris 434 and flows near the sidewalls as the laminar streams 436 and 438, is diverted to the side outlet port 420 through the pair of side outlet channels 422.

After the acoustic sorting process is completed, the fourth container or bag 110 containing the genetically modified target cells with may be severed from the rest of the integrated system 600 without exposing its content to atmosphere. The content in the fourth container or bag 110 may be intravenously administered to patients.

FIG. 9 is a frontal view of the integrated system 600 that may be used to produce CAR T cells from whole blood or samples containing T cells in accordance with the process described above. The system 600 may utilize a closed fluidic assembly to become a closed processing system that can be deployed in a facility that lacks a stringent sterile or clean environment, such as the treatment facility, thereby alleviating much of the common logistic issues encountered in the autologous treatment.

FIG. 9 shows the automated production system 600 including a shell or housing structure 140, first and second magnetic separator modules 142A, 142B and an acoustic separator module 310 residing in the housing structure 140, an incubation module 144, a sample rack 146 mounted on top of the housing structure 140, and first and second sample bag holders 164, 166. The fluidic lines and sample bags connected thereto, which may be supplied as an integrated disposable tubing set, and the computer used for controlling the system 600 are omitted in the drawing in order to present an unobstructive view of the magnetic separator modules 142A, 142B and the acoustic separator module 310. The production system 600 is analogous to the systems 300, 500 except for the routing of the fluidic lines as will be shown below.

The incubation module 144 includes an incubation chamber 106 sitting on top of a rocker base 147. Each of the magnetic separator modules 142A, 142B includes a first pinch valve 148A, 148B, a second pinch valve 150A, 150B, a third pinch valve 152A, 152B, a fourth pinch valve 154A, 154B, a first air detector 156A, 156B, a second air detector 158A, 158B, a peristaltic pump 160A, 160B, a blockage sensor 162A, 162B, and a magnetic separator device 104, 105. The acoustic separator module 310 includes first and second peristaltic pumps 312, 314, first and second blockage sensors 316, 318, first and second air detectors 320, 322, an acoustic separator device 302, first, second, and third pinch valves 324-328.

The system 600 may also include additional pinch valves 168, 170, 608 disposed on one side of the housing structure 140 and additional pinch valves 172, 174 disposed on the other side of the housing structure 140. The electromechanical components 104-106, 147, 148A/B-162A/B, 168-174, 312-328, 608 may be controlled or automated by a computer or microprocessor (not shown).

Each of the magnetic separator devices 104, 105 may have a structure that is identical or substantially similar to the magnetic separator device 188 shown in FIGS. 3 and 4 and described above. Other magnetic flux sources and column-free magnetic separator devices, such as those disclosed in U.S. application Ser. No. 18/072,362, which is incorporated herein by reference, may also be used to separate the magnetically labeled target cells from the fluid sample.

The acoustic separator device 302 may have a structure that is identical or substantially similar to the acoustic separator device 428 shown in FIGS. 8A-8E and described above.

The incubation module 144 includes the cell incubation chamber 106 sitting atop of the rocker base 147. The incubation chamber 106 has a heater that can uniformly maintain the temperature inside the chamber 106 between room temperature and 50° C. The $CO_2$ concentration inside the chamber 106 can be varied between 0 and 10% to provide an optimal environment for cells. The rocker base 147 may move the chamber 106 at a speed between 2 rpm and 4 rpm. The swaying motion of the chamber 106 caused by the rocker base 147 may facilitate uniform mixing of the fluid content inside the cell container 134. The rocker base 147 may remain stationary during cell activation, transduction, or expansion process. After the incubation process, the rocker base 147 may effectuate the cell container 134 inside the chamber 106 to sway, causing the fluid in the cell container 134 to rinse cells off the surface of the cell container 134. The rocker base 147 may also be used to facilitate draining of the cell container 134 by tilting the incubation chamber 106 to a fixed position to allow the end of the outlet tube to reach the bottom of the fluid inside the cell container 134.

The system 600 has a modular design comprising two magnetic separator modules 142A, 142B, one acoustic separator module 310, and one incubation module 144. The modules 142A, 142B, 144, and 310 may be fluidically connected in series, parallel, or a combination thereof by a closed fluidic assembly that includes sample bags, cell containers, acoustic separator device, and all fluidic lines including conduits passing through the magnetic separator devices.

Figure 16:
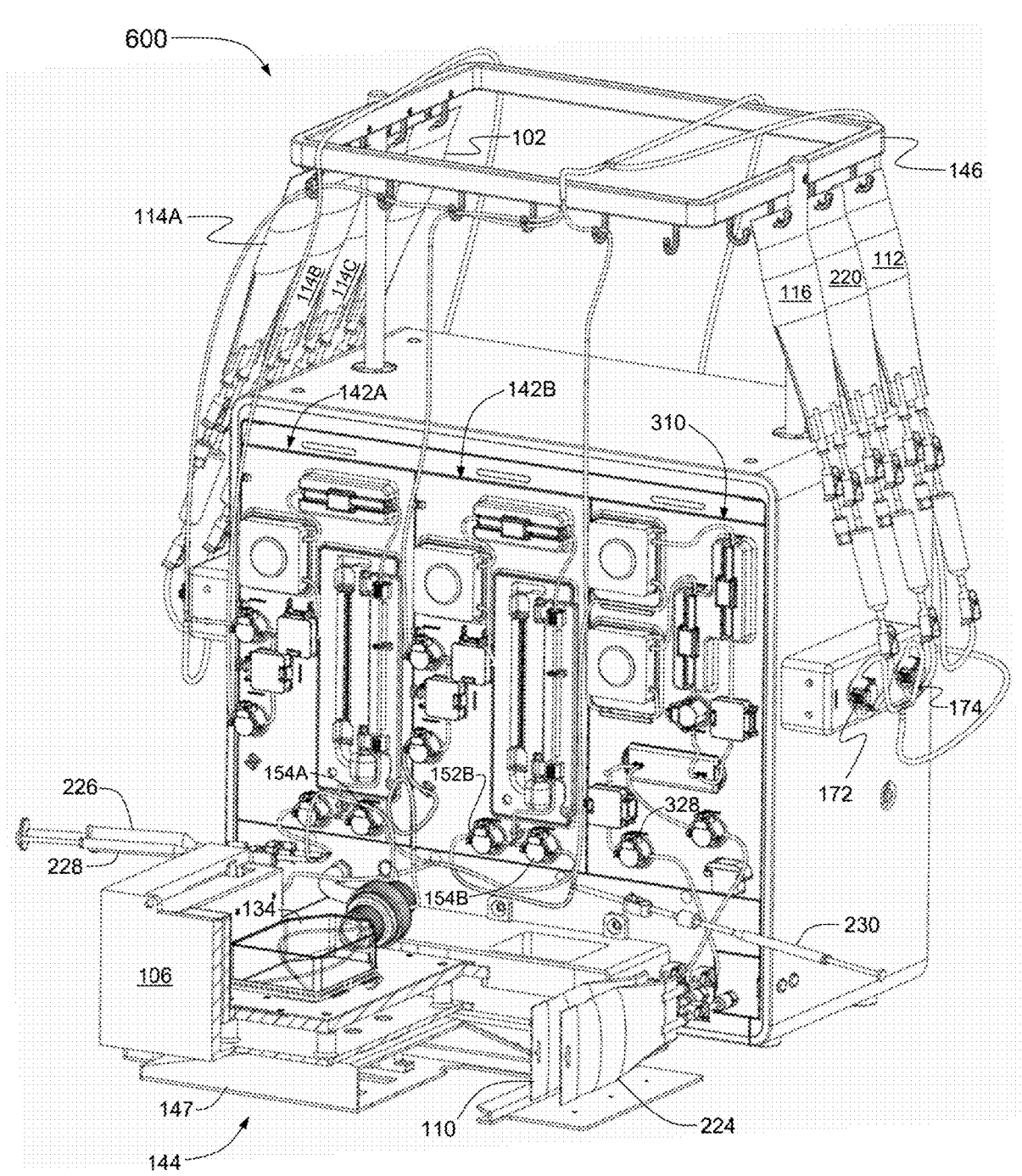
FIG. 16 is a perspective view of the integrated system of FIG. 9 using a closed fluidic assembly in the form of an integrated tubing set for manufacturing CAR T cells in accordance with the fourth embodiment of the present invention.
Figure 17:
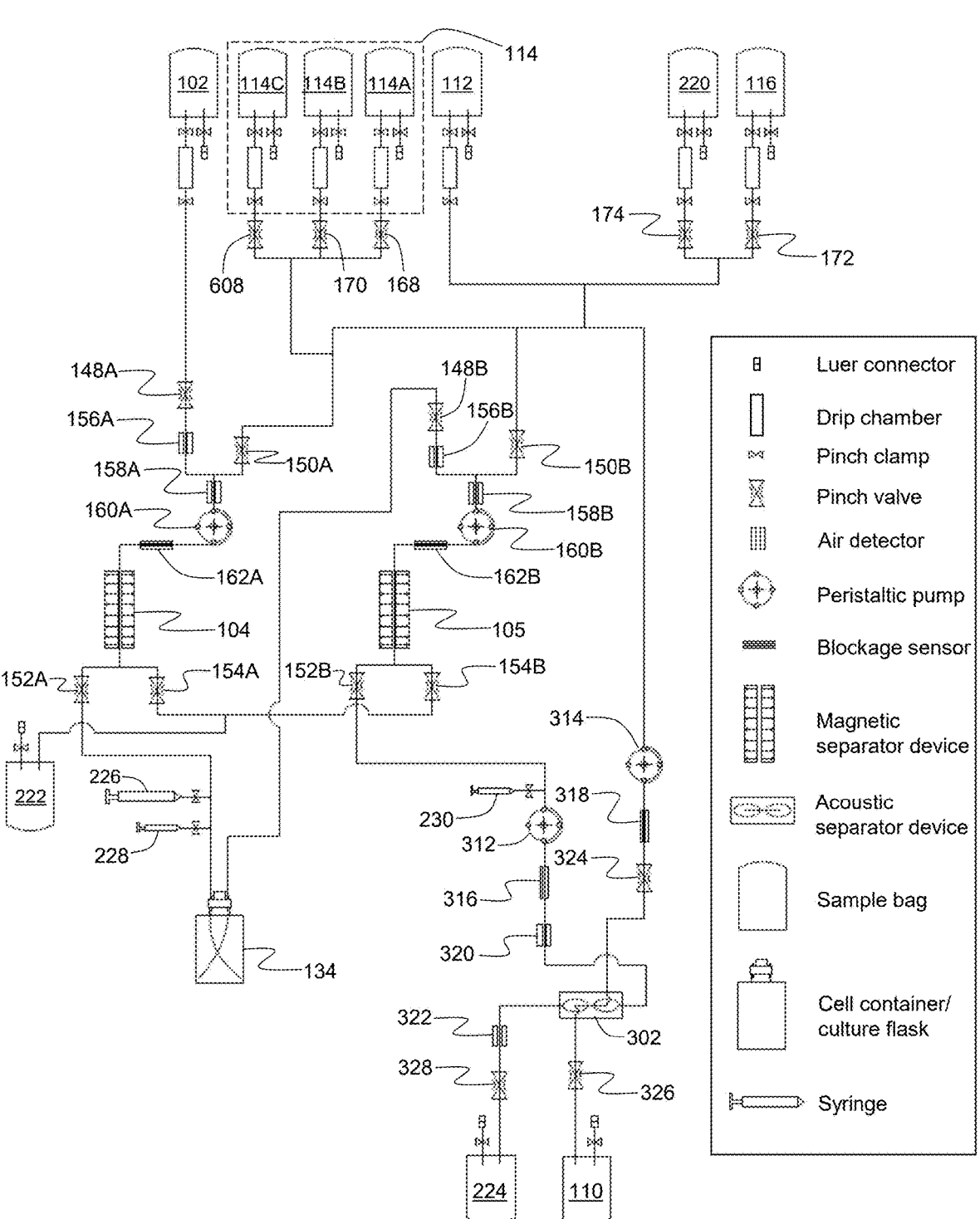
FIG. 17 is fluidic circuit diagram corresponding to the integrated system of FIG. 16.

FIG. 16 is a perspective view of the system 600 using a closed fluidic assembly in the form of an integrated tubing set for manufacturing CAR T cells. For reasons of legibility, electromechanical components labeled in FIG. 9 are not relabeled in the drawing to clearly show the routing of fluidic lines. The perspective view also shows the pinch valves 152B, 154A, 154B, 328 that are previously blocked by the cell incubation chamber 106 and the pinch valves 172, 174 disposed on one side of the housing structure 140 in the frontal view of FIG. 9. The lid and a section of the side wall of the incubation chamber 106 are further removed to expose the cell container 134 in the form of a common cell culture flask inside the chamber 106. The cap of the cell culture flask 134 contains an air filter that is vented to the environment inside the incubation chamber 106 while preserving sterility inside the flask 134. The second bag holder 166 is also omitted from the drawing to show the sample bags 110, 224 inside the holder 166. FIG. 17 is a fluidic circuit diagram corresponding to the system 600 shown in FIG. 16.

Referring to FIGS. 9, 16, 17, the fluidic assembly of the system 600, in contrast to the fluidic assemblies of systems 100, 300, 500, is not arranged to use both the first and second magnetic separator devices 104, 105 to extract the magnetically labeled target cells from the first fluid sample in the magnetic sorting process. The first magnetic separator device 104 is used for extracting the magnetically labeled target cells from the first fluid sample while the second magnetic separator device 105 is used to remove the free magnetic labels after the magnetic labels are removed from the target cells. The acoustic separator device 302 is then used for purifying nonmagnetic target cells.

The first, second, third, and fourth containers or bags 102, 112, 116, 110 are in the form of sample bags. The sample bags 102 and 112 are both fluidically connected to the inlet of the first magnetic separator devices 104. In addition to the sample bag 116, another sample bag 220, which may also contain cryopreservation solution, storage media, PBS based solution, saline based solution, human serum, glucose, or any combination thereof, is also fluidically connected to the inlet of the acoustic separator device 302. The incubation ingredient bank 114 includes at least three sample bags 114A-114C fluidically connected to the cell container 134 through the magnetic separator device 104. Each of the sample bags 114A, 114B, 114C may include culture media, vectors for cell transduction or transfection, lentivirus for transduction, buffers or solutions for non-viral transfection, cell activation reagent, or reagent for stripping magnetic labels from the target cells (i.e., delabeling reagent). Prior to the transduction or transfection process, the target T cells in the cell container 134 may be activated by flowing a cell activation reagent (e.g., solution containing CD3/CD28 magnetic beads) from one of the sample bags 114A-114C into the cell container 134.

The fluidic assembly of the system 600 further includes a sample bag 222 fluidically connected to the outlets of the first and second magnetic separator devices 104, 105 for collecting waste from the devices 104, 105, and another sample bag 224 fluidically connected to the outlet of the acoustic separator device 302 for collecting waste from the device 302. The sample bag 222 for collecting waste from the first and second magnetic separator devices 104, 105 may be placed in the first bag holder 164. The sample bags 110, 224 for respectively collecting the final cell product and waste from the acoustic separator device 302 may be placed in the second bag holder 166. All other sample bags 102, 112, 114A-114C, 116, 220, which provide materials for the manufacturing process, may be hung on the sample rack 146. The fluidic assembly of the system 600 may include additional sample bags for various purposes. Each of the sample bags 102, 110, 112, 114A-114C, 116, 220-224 may have an inlet port with a Luer connector connected thereto and an outlet port with a drip chamber connected thereto. Additionally, the fluid flowing through the inlet and outlet ports of each sample bag may be controlled or regulated by one or more manual pinch clamps attached thereto.

The fluidic assembly of the system 600 may also include syringes 226, 228, 230. The syringes 226, 228, which may be fluidically connected to the inlet of the cell container 134, may be used to extract a sample of the magnetically separated target cells after the magnetic sorting process or may inject culture media, vectors for cell transduction or transfection, lentivirus for transduction, buffers or solutions for non-viral transfection, cell activation reagent, or delabeling reagent into the cell container 134. The syringe 230, which may be fluidically connected to the outlet of the cell container 134 or the outlet of the second magnetic separator device 105, may be used to extract a sample of the genetically modified target cells after the transduction or transfection process is completed.

With continued reference to FIG. 17, the fluidic circuit corresponding to the system 600 includes the sample bags 102, 110, 112, 114A-114C, 116, 220-224, the syringes 226-230, the cell container 134, and the acoustic separator device 302, all interconnected by a network of fluidic lines that pass through the electromechanical components, such as the pinch valves 148A/B-154A/B, 168-172, 324-328, the air detectors 156A/B, 158A/B, 320, 322, the blockage sensors 162A, 162B, 316, 318, the peristaltic pumps 160A, 160B, 312, 314, and the magnetic separator devices 104, 105. The sample bags 102, 110, 112, 114A-114C, 116, 220-224, the syringes 226-230, the cell container 134, the acoustic separator device 302, and the network of fluidic lines including the conduits passing through the magnetic separator devices 104, 105 may be constructed, interconnected, sterilized, and supplied as an integrated disposable set. The electromechanical components of the system 600 are external to the tubing set and therefore do not come into contact the fluid in the tubing set.

The first container or sample bag 102, which may contain target cells for processing, is fluidically connected to the inlet of the conduit passing through the first magnetic separator device 104 by one or more fluidic lines that pass through the first pinch valve 148A, the first air detector 156A, the second air detector 158A, the peristaltic pump 160A, and the blockage sensor 162A. The second container or sample bag 112, which may contain a buffer solution or culture media, is fluidically connected to the inlet of the conduit passing through the first magnetic separator device 104 by one or more fluidic lines that pass through the second pinch valve 150A, the second air detector 158A, the peristaltic pump 160A, and the blockage sensor 162A, and is also fluidically connected to the inlet of the conduit passing through the second magnetic separator device 105 through one or more fluidic lines that pass through the second pinch valve 150B, the second air detector 158B, the peristaltic pump 160B, and the blockage sensor 162B. In this arrangement shown, the first and second magnetic separator devices 104, 105 uses the same buffer or culture media solution stored in the second container or sample bag 112 instead of separate containers or sample bags 112, 602 as shown in FIG. 15. However, a separate container or sample bag 602 may be fluidically connected to the inlet of the conduit passing through the second magnetic separator device 105 for eluting the free magnetic labels collected by the device 105.

The inlet of the cell container 134 is fluidically connected to the outlet of the conduit passing through the first magnetic separator device 104 by one or more fluidic lines that pass through the third pinch valve 152A. The syringes 226, 228 may be fluidically connected to a fluidic line between the inlet of the cell container 134 and the third pinch valve 152A. The sample bag 222, which may store waste fluid containing non-target cells and/or free magnetic labels, is fluidically connected to the outlet of the conduit passing through the first magnetic separator device 104 by one or more fluidic lines that pass through the fourth pinch valve 154A, and is also fluidically connected to the outlet of the conduit passing through the second magnetic separator device 105 by one or more fluidic lines that pass through the fourth pinch valve 154B.

The outlet of the cell container 134 is fluidically connected to the inlet of the conduit passing through the second magnetic separator device 105 by one or more fluidic lines that pass through the first pinch valve 148B, the first air detector 156B, the second air detector 158B, the peristaltic pump 160B, and the blockage sensor 162B.

The outlet of the conduit passing through the second magnetic separator device 105 is fluidically connected to the inlet of the acoustic separator device 302 (e.g., side inlet port 412 of FIG. 8A) by one or more fluidic lines that pass through the third pinch valve 152B, the first peristaltic pump 312, the first blockage sensor 316, and the first air detector 320. The syringe 230 may be fluidically connected to a fluidic line connected to the outlet of the cell container 134 or the outlet of the conduit passing through the second magnetic separator device 105 as shown. The third container or sample bag 116 is fluidically connected to the inlet of the acoustic separator device 302 (e.g., center inlet port 416 of FIG. 8A) by one or more fluidic lines that pass through the pinch valve 172, the second peristaltic pump 314, the second blockage sensor 318, and the first pinch valve 324. The sample bag 220 is fluidically connected to the inlet of the acoustic separator device 302 (e.g., center inlet port 416 of FIG. 8A) by one or more fluidic lines that pass through the pinch valve 174, the second peristaltic pump 314, the second blockage sensor 318, and the first pinch valve 324.

The fourth container or sample bag 110 is fluidically connected to the outlet of the acoustic separator device 302 (e.g., center outlet port 424 of FIG. 8A) by one or more fluidic lines that pass through the second pinch valve 326. The sample bag 224, which may be used to receive waste fluid, is fluidically connected to the outlet of the acoustic separator device 302 (e.g., side outlet port 420 of FIG. 8A) by one or more fluidic lines that pass through the second air detector 322 and the third pinch valve 328.

The sample bag 114A of the incubation ingredient bank 114 is fluidically connected to the inlet of the cell container 134 by one or more fluidic lines that pass through the pinch valve 168, the second pinch valve 150A, the second air detector 158A, the peristaltic pump 160A, the blockage sensor 162A, the first magnetic separator device 104, and the third pinch valve 152A. The sample bag 114B of the incubation ingredient bank 114 is fluidically connected to the inlet of the cell container 134 by one or more fluidic lines that pass through the pinch valve 170, the second pinch valve 150A, the second air detector 158A, the peristaltic pump 160A, the blockage sensor 162A, the first magnetic separator device 104, and the third pinch valve 152A. Similarly, the sample bag 114C of the incubation ingredient bank 114 is fluidically connected to the inlet of the cell container 134 by one or more fluidic lines that pass through the pinch valve 608, the second pinch valve 150A, the second air detector 158A, the peristaltic pump 160A, the blockage sensor 162A, the first magnetic separator device 104, and the third pinch valve 152A.

As understood by those skilled in the art, the processes described in Embodiments 1-4 can be practiced using other systems or instruments not described herein. For example, the initial magnetic isolation/extraction of T cells and/or the final magnetic harvesting/purification may be performed using a column-based magnetic separator device; or the magnetic separator devices, the acoustic separator device, the cell container may not be fluidically connected or integrated into a system (i.e., discrete instruments).

EXAMPLES

The following examples are provided to illustrate, but do not limit the invention.

The recovery rate of target cells reported herein is calculated from the number of events or cells for the target cells in the fluid sample after magnetic or acoustic sorting divided by the number of events or cells for the target cells in the initial fluid sample prior to any sorting, as measured by a flow cytometer (CytoFlex, Beckman Coulter). The purity of the target cells reported herein is calculated from the number of events or cells for the target cells divided by the number of all events or cells in the fluid sample, as measured by the flow cytometer.

Example 1: CAR T Cells Produced from Fresh Leukopak Using Positive Magnetic Isolation and Positive Magnetic Purification This example uses the system 100 equipped with a closed fluidic assembly as shown in FIGS. 2, 5, 6 and describe above. The system 100 includes three magnetic modules 142A-142C and an incubation module 144. The closed fluidic assembly includes the sample bags 102, 110, 112, 114A, 114B, 116, 220-224, the cell container 134 in the form of a cell culture flask, the conduits that pass through the magnetic separator devices 104, 105, 108, and fluidic lines that connect these components.

The sample preparation process begins by incubating a leukapheresis sample consisting of about 1/10 of a leukopak, which contains ~6×10^8 cells, with CD4/CD8 magnetic beads (Beijing T&L Biological Technology) to magnetically label the T cells at room temperature for 30 min while rocking on a mixer. After incubation, the leukapheresis sample is diluted with a buffer fluid (MARS® MAG Buffer, Applied Cells) to a cell concentration of ~3×10^7 cells/ml and a total volume of ~20 ml, yielding the first fluid sample, which is then transferred to the first sample bag 102. It worth noting that T cells can also be extracted or isolated directly from whole blood using the magnetic separator device shown in FIGS. 3 and 4 without leukapheresis or buffy coat extraction, as reported in U.S. patent application Ser. No. 18/795,047, which is incorporated herein by reference in its entirety.

The isolation or extraction of the T cells from the first fluid sample begins by flowing the first fluid sample from the first sample bag 102 through the pair of magnetic separator devices 104, 105 at a total flow rate 1 ml/min. As the first fluid sample flows through the magnetic separator devices 104, 105, the magnetically labeled T cells are retained in the devices 104, 105 by magnetic fields, while the depleted first fluid sample exits the devices 104, 105 and is collected by the sample bag 222. After the first fluid sample completely passes through the magnetic separator devices 104, 105, the magnetic fields acting on the magnetically labeled T cells are removed, and a first eluant, comprising a T cell culture medium (OptiVitro, ExcellBio) with IL-2 (300 IU/ml), IL-7 (10 ng/ml), and IL-15 (10 ng/ml) (TL), flows from the second sample bag 112 to the magnetic separator devices 104, 105 to elute the magnetically labeled T cells into the cell culture flask 134, which is disposed inside the cell incubation chamber 106.

Figure 18A:
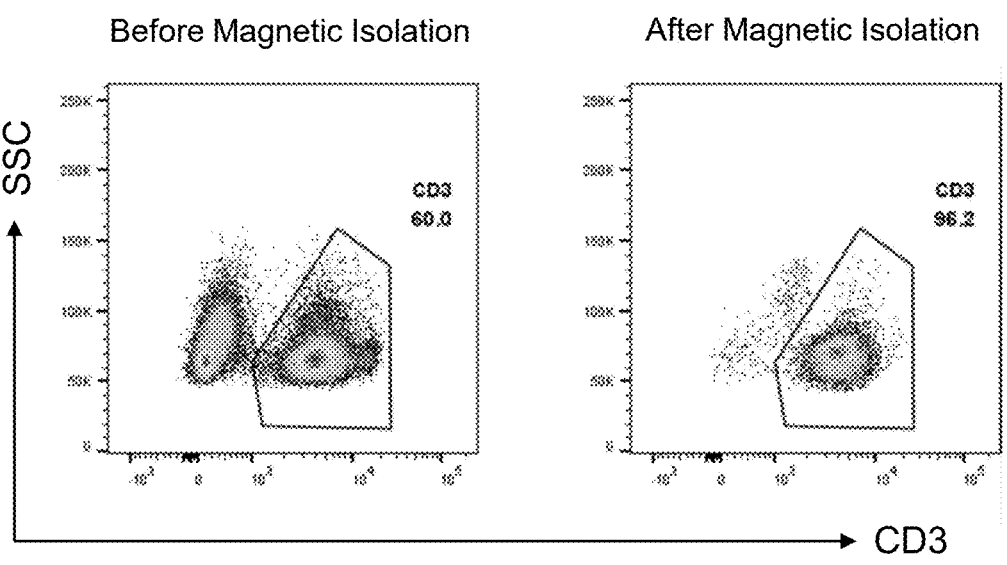
FIGS. 18A and 18B are dot plots showing T cell purity before and after the magnetic isolation process from a leukopak sample.
Figure 18B:
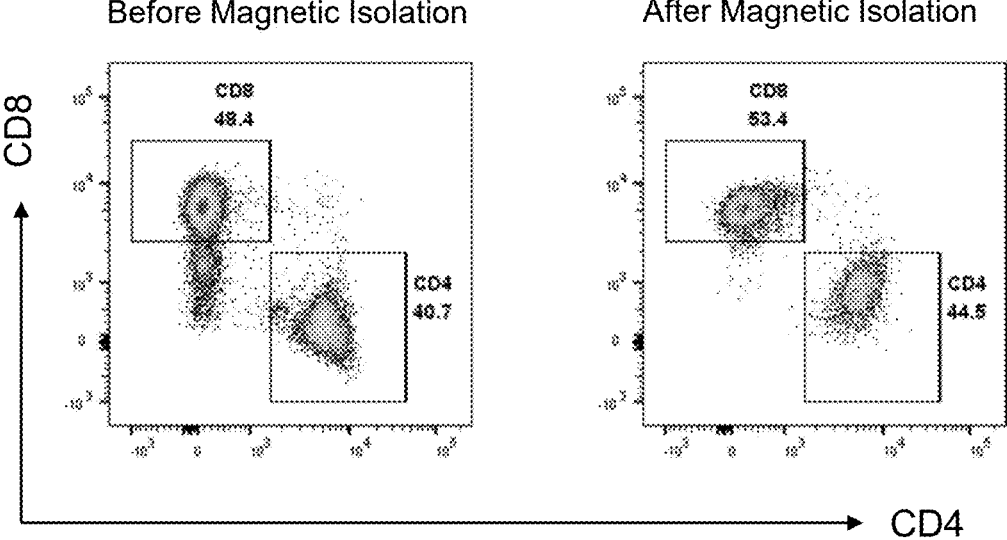

FIG. 18A shows dot plots of the first fluid sample, which comprises the initial leukopheresis sample before the magnetic isolation process, and the culture medium containing the T cells extracted from the magnetic isolation process. The cytometry data shows that the magnetic isolation process increases the purity of the T cells, as a percentage of overall white blood cells, from 60% to 96%, and 59% of the T cells are recovered (i.e., recovery ratio) from the magnetic isolation process. The cytometry data of FIG. 18B further shows that the CD4⁺/CD8⁺ ratio of the T cells remains relatively constant after the magnetic isolation process.

After the magnetic isolation process, the process of activating the T cells in the cell culture flask 134 begins by flowing a activation reagent, comprising ActCel CD3/CD28 magnetic beads (Beijing T & L Biological Technology) diluted with the T cell culture medium, from the sample bag 114A to the cell culture flask 134. After addition of the activation reagent to the cell culture flask 134, the cell incubation chamber 106 is swayed on the rocker base 147 to uniformly mix the fluid mixture inside the cell culture flask 134. The T cells are then incubated with the CD3/CD28 magnetic beads in the cell culture flask 134 at 37° C. for 24 hours in a 5% $CO_2$ environment inside the cell incubation chamber 106.

Figure 19:
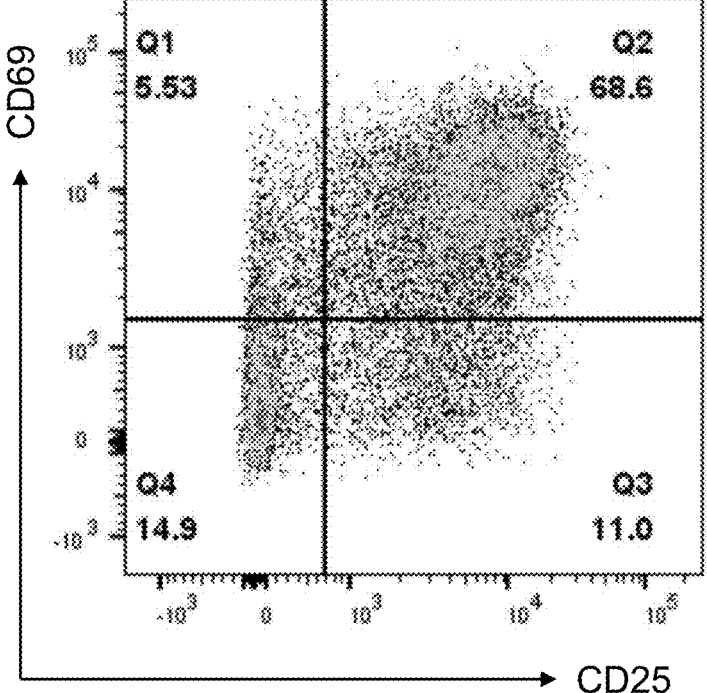
FIG. 19 is a dot plot showing activation of T cells after incubated with CD3/CD28 magnetic beads for 24 hours.

FIG. 19 is a dot plot showing the expression of activation markers CD25 and CD69 on the T cells incubated with the CD3/CD28 magnetic beads for 24 hours. The plot shows 80%, 74%, and 69% of T cells express CD25, CD69, and CD25+CD69 (double positive) activation markers, respectively.

After the activation process, the process of transducing the T cells in the cell culture flask 134 begins by flowing a lentivirus solution, comprising CD19 CAR-T lentivirus (Jiangsu Hillgene BioPharma Co., Ltd.) suspended in the T cell culture medium, from the sample bag 114B to the cell culture flask 134 at a multiplicity of infection (MOI) ratio of 5. After addition of the lentivirus solution to the cell culture flask 134, the cell incubation chamber 106 is swayed on the rocker base 147 to uniformly mix the fluid mixture inside the cell culture flask 134. The T cells are then incubated with the lentivirus in the cell culture flask 134 at 37° C. for 24 hours in the 5% $CO_2$ environment inside the cell incubation chamber 106.

After the transduction process, the harvesting/purification process of the T cells begins by flowing the second fluid sample in the cell culture flask 134, which comprises the T cells and residual lentivirus, through the magnetic separator devices 108 at a flow rate 0.5 ml/min. As the second fluid sample flows through the magnetic separator device 108, the magnetically labeled T cells are retained in the device 108 by the magnetic field, while the depleted second fluid sample containing residual lentivirus exits the device 108 and is collected by the sample bag 224. After the second fluid sample completely passes through the magnetic separator device 108, the magnetic field acting on the magnetically labeled T cells is removed, and a second eluant, comprising the buffer fluid (MARS® MAG Buffer, Applied Cells), flows from the third sample bag 116 to the magnetic separator device 108 to elute the T cells into the fourth sample bag 110 for subsequent analysis, including cytometry. The magnetic harvesting/purification process recovers 91% of the T cells from the second fluid sample after the activation and transduction processes. Alternatively, a cryopreservation solution stored in the sample bag 220 may be used as the second eluant to preserve the T cells in the fourth sample bag 110 for cryopreservation.

Figure 20A:
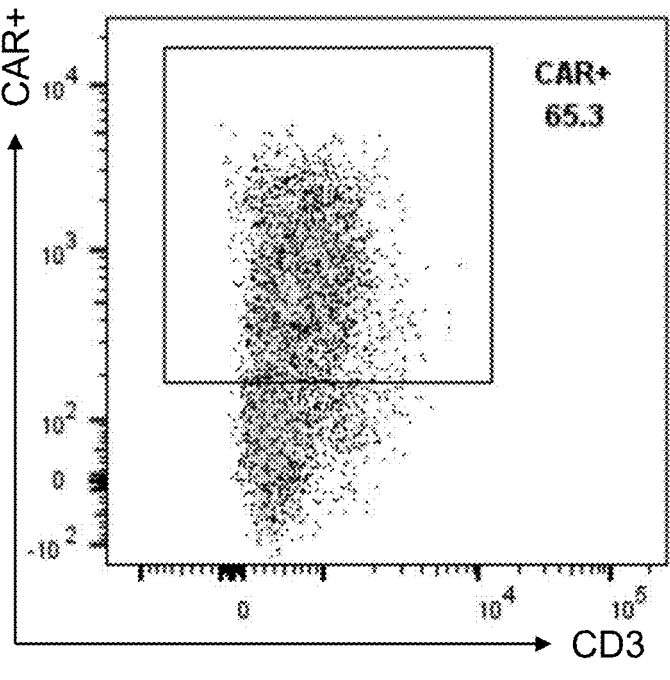
FIGS. 20A and 20B are dot plots for transduced T cells after magnetic harvesting.
Figure 20B:
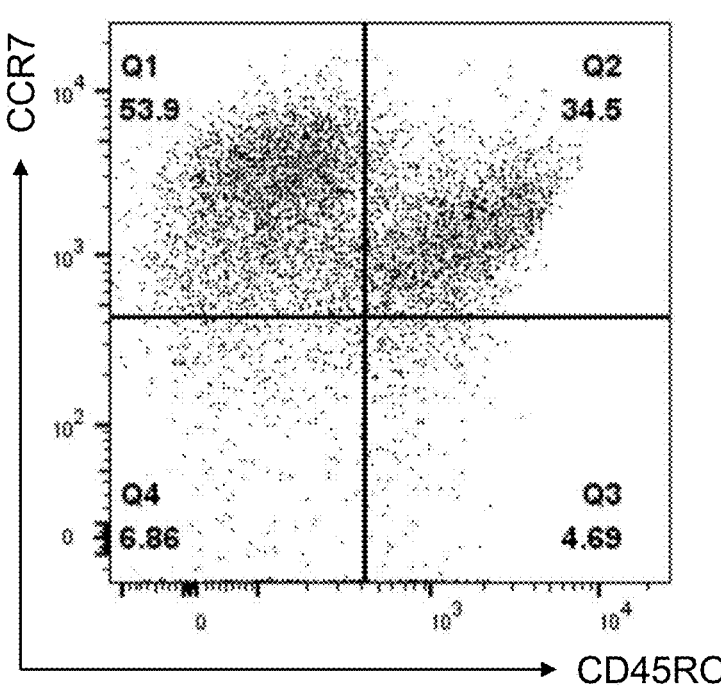

FIGS. 20A and 20B are dot plots corresponding to the final T cell product after the transduction process and the magnetic harvesting/purification process. FIG. 20A shows that 65% of T cells express the CAR. Furthermore, FIG. 20B shows that 88% of the CAR T cells express CCR7 marker (memory T cells) and, more particularly, 54% of the CAR T cells are T stem cell memory (TSCM) cells. The percentage of TSCM cells produced by the current method is notably higher than the convention production method that requires the expansion of T cells.

While the present invention has been shown and described with reference to certain preferred embodiments, it is to be understood that those skilled in the art will no doubt devise certain alterations and modifications thereto which nevertheless include the true spirit and scope of the present invention. Thus the scope of the invention should be determined by the appended claims and their legal equivalents, rather than by examples given.

Any element in a claim that does not explicitly state "means for" performing a specified function, or "step for" performing a specific function, is not to be interpreted as a "means" or "step" clause as specified in 35 U.S.C. § 112, 16. In particular, the use of "step of" in the claims herein is not intended to invoke the provisions of 35 U.S.C. § 112, 16.

What is claimed is:

1. A method for producing a population of T cells that express a chimeric antigen receptor (CAR) comprising the steps of:

providing a fluid sample including a population of T cells;

labeling the population of T cells with magnetic beads;

extracting the population of T cells from the fluid sample by flowing the fluid sample through a first conduit that passes through a first magnetic separator device;

transducing or transfecting the population of T cells to express a chimeric antigen receptor (CAR) by contacting the population of T cells with a population of lentivirus in a solution contained in an incubation container; and harvesting the population of T cells by flowing the solution through a second conduit that passes through a second magnetic separator device, wherein the first conduit, the incubation container, and the second conduit are fluidically connected by a network of fluidic lines, and wherein the first and second magnetic separator devices each comprise:

a center magnetic flux guide including a center tip having a tapering shape and a center base;

a first side magnetic flux guide including a first side tip and a first side base;

a second side magnetic flux guide including a second side tip and a second side base, the first and second side magnetic flux guides being disposed on opposite sides of the center magnetic flux guide;

a magnetic flux source generating magnetic flux in the center magnetic flux guide and the first and second side magnetic flux guides; and a floating magnetic flux guide that operably pushes the first or second conduit against the center tip and the first and second side tips.

2. The method of claim 1, wherein the magnetic flux source includes a first permanent magnet disposed between the first side magnetic flux guide and the center magnetic flux guide and a second permanent magnet disposed between the second side magnetic flux guide and the center magnetic flux guide, and wherein the first and second permanent magnets have opposite magnetization directions.

* * * * *